United States Patent [19]

Krapcho et al.

[11] Patent Number: 5,604,246
[45] Date of Patent: Feb. 18, 1997

[54] 2-AMINOALKYL-5-AMINOALKYLAMINO SUBSTITUTED-ISOQUINOINDAZOLE-6(2H)-ONES

[75] Inventors: A. Paul Krapcho, Shelburne, Vt.; Ernesto Menta, Milan, Italy; Ambrogio Oliva, Verese, Italy; Silvano Spinelli, Milan, Italy

[73] Assignees: Boehringer Mannheim Italia SpA, Monza, Italy; Univ. of Vermont, Burlington, Vt.

[21] Appl. No.: 350,843

[22] Filed: Dec. 7, 1994

Related U.S. Application Data

[62] Division of Ser. No. 103,641, Aug. 11, 1993, Pat. No. 5,519,029.

[51] Int. Cl.⁶ .......... A61K 31/445; C07D 239/02
[52] U.S. Cl. .......... 514/318; 544/125; 544/333; 544/361; 546/63; 546/64; 546/101; 514/185; 514/232.8; 514/253; 514/398; 514/399; 514/400; 514/406; 514/422; 514/286; 514/287

[58] Field of Search .......... 544/125, 333, 544/361; 546/63, 64, 101; 514/185, 232.8, 253, 318, 398, 399, 400, 406, 422, 286, 287

[56] References Cited

U.S. PATENT DOCUMENTS 5,447,950  9/1995  Patterson .......... 514/406

OTHER PUBLICATIONS

Showalter, et al *J. Med. Chem.* (1987), 30 pp. 121–131.
Talbot, et al. *J. Clin Oncol.* (1991), 9(12) pp. 2141–2147.
Campling, et al in *Nephrotoxicity*, Peter H. Dekker Bach, ed., (New York 1992) pp. 345–352.

*Primary Examiner*—Kimberly J. Prior
*Attorney, Agent, or Firm*—Nikaido, Marmelstein, Murray & Oram LLP

[57] ABSTRACT

This invention is directed to 2-aminoalkyl-5-aminoalkylamino substituted isoquino[8,7,6-cd]indazole-6-(2H)-ones and to 2-aminoalkyl-5-aminoalkylamino substituted-isoquino[5,6,7-cd]indazole-6(2H)-ones. These compounds have been shown to have antitumor activity.

6 Claims, 4 Drawing Sheets

2-AMINOALKYL-5-AMINOALKYLAMINO SUBSTITUTED-ISOQUINOINDAZOLE-6(2H)-ONES

This application is a divisional of application Ser. No. 08/103,641, filed Aug. 11, 1993, now U.S. Pat. No. 5,519,029.

BACKGROUND OF THE INVENTION

1. Field of the Invention

This invention is directed to azaanthrapyrazoles, namely to 2-aminoalkyl-5-aminoalkylamino substituted isoquino[8,7,6-cd]indazole-6-(2H)-ones and to 2-aminoalkyl-5-aminoalkylamino substituted-isoquino[5,6,7-cd]indazole-6(2H)-ones. These compounds have been shown to have antitumor activity.

2. Background

Certain 1,4-bis[(aminoalkyl)amino]anthracene-9,10-diones have been reported which show antitumor activity in clinical trials. Of particular interest has been ametantrone, 1,4-bis{[2-(2-hydroxyethylamino)ethyl]amino}anthracene-9,10-dione, and mitoxantrone, 5,8-dihydroxy-1,4-bis{[2-(2-hydroxyethylamino)ethyl]amino}anthracene-9,10-dione. [Zee-Cheng et al., J. Med. Chem. 21, 291–4 (1978); Cheng et al., "Progress in Medicinal Chemistry", Ellis, G. P. and West, G. B., eds.; Elsevier: Amsterdam, 1983, Vol. 20, pp. 83 and references cited therein]. Mitoxantrone is a broad spectrum oncolytic agent, whose activity is similar to that of the anthracycline antibiotic doxorubicin. Clinical trials have demonstrated that mitoxantrone has particularly promising activity in the treatment of advanced breast cancer, acute leukemia and lymphoma [Legha, Drugs of Today, 20, 629 (1984)]. Although animal studies have demonstrated a diminished cardiotoxicity in comparison to doxorubicin, some clinical cardiotoxicity has been observed also with mitoxantrone, mostly in patients previously treated with doxorubicin (R. Stuart Harris et al., Lancet, 219, (1984) and references cited therein). Ametantrone has been reported to be, in animals, about 10-fold less potent and less cardiotoxic than mitoxantrone. Because a delayed toxicity is observed only with mitoxantrone after administration of the two drugs by the i.p. route to non-tumor bearing rats at equieffective antitumor dosages, it is suggested that the presence of the 5,8-dihydroxy substitution in mitoxantrone might be implicated in the delayed deaths [Corbett et al., Cancer Chemother. Pharmacol., 6, 161, (1981)].

In addition, both mitoxantrone and ametantrone have a remarkable myelodepressive toxicity and both compounds show cross-resistance to cell histotypes developing resistance against doxorubicin mediated by overexpression of glycoprotein P. Such a resistance, which is named multidrug resistance, involves a number of antitumor antibiotics, among which are amacrine and podophyllotoxinic derivatives, and this resistance is one of the main reasons for therapeutical failures in the treatment of solid tumors with such antibiotics.

In an attempt to overcome the above mentioned drawbacks, some chromophore modified anthracenediones have been prepared. For example, E.P. Patent Application 103,381 discloses 2-aminoalkyl-5-aminoalkylamino substituted anthra[1,9-cd]pyrazol-6(2H)-ones (anthrapyrazoles) which are claimed to have antitumor activity. The antitumor activity of said compounds in a number of preclinical models has been reported by H. D. Hollis Showalter et al. [J. Med. Chem., 30, 121–131, (1987)]. However, anthrapyrazoles are not devoid of toxic side effects, with severe leukopenia (W.H.O. grade 3 and 4) and neutropenia (W.H.O. grade 4) being dose limiting in phase I and phase II clinical trials with the anthrapyrazole CI-941 [I. E. Smith et al., J. Clin. Oncol. 9, 2141–2147, (1991)]. Moreover, a marked nephrotoxicity is associated with CI-941 treatment in the rat [D. Campling and M. E. C. Robbins, Nephrotoxicity, Peter H. Dekker Bach editor, pp. 345–352, (1991), New York; see Chemical Abstract 116:294n, (1992)], and these authors suggest that renal injury may be a clinical problem with anthrapyrazole therapy.

Therefore, the search for newer active analogues is still highly desirable.

We have now discovered that the introduction of one nitrogen atom in the position 9 or in the position 8 of the above mentioned anthra[1,9-cd]pyrazol-6(2H)-ones provides 2-aminoalkyl-5-aminoalkylamino substituted isoquino[8,7,6-cd]indazole-6-(2H)-ones and 2-aminoalkyl-5-aminoalkylamino substituted-isoquino[5,6,7-cd]indazole-6(2H)-ones respectively, which are endowed with marked antitumor activity.

BRIEF SUMMARY OF THE INVENTION

The compounds of the invention have the formula (I):

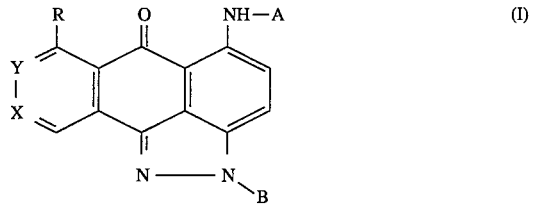

wherein R is hydrogen or hydroxy;

one of X and Y is a carbon atom and the other is a nitrogen atom, with the proviso that when Y is nitrogen, R is hydrogen;

A and B are the same or different and are selected from the group of $C_1$–$C_{10}$ alkyl or [phenylalkyl]; $C_2$–$C_{10}$ alkyl having one or two substituents selected from the group consisting of $OR_1$ and $NR_2R_3$; $C_2$–$C_{10}$ alkyl interrupted by one or two oxygen atoms or by one —$NR_4$— group, and said $C_2$–$C_{10}$ alkyl is optionally substituted by one or two hydroxy (OH) or $NR_2R_3$ groups;

$R_1$ is selected from the group consisting of hydrogen, $C_1$–$C_6$ alkyl, phenyl, [phenylalkyl], —$S(O_2)R_5$, $C_2$–$C_6$ alkyl optionally substituted by $NR_2R_3$;

$R_2$ and $R_3$ may be the same or different and are selected from the group consisting of hydrogen, $C_1$–$C_{10}$ alkyl, [phenylalkyl], phenyl, $C_2$–$C_{10}$ alkyl substituted with one or two hydroxy (OH) groups, or $R_2$ and $R_3$ taken together with the nitrogen atom to which they are bound form an ethyleneimine ring or a 5- or 6-member aromatic or non-aromatic heterocyclic ring which optionally contains another heteroatom such as sulfur, oxygen or nitrogen;

$R_4$ is selected from the group consisting of hydrogen, $C_1$–$C_{10}$ alkyl, $C_2$–$C_{10}$ hydroxyalkyl, $C_2$–$C_{10}$ alkyl substituted with $NR_2R_3$, [phenylalkyl], phenyl;

$R_5$ is selected from the group consisting of $C_1$–$C_{10}$ alkyl, [phenylalkyl], as free bases and their salts with pharmaceutically acceptable acids.

The present invention also concerns the tautomeric forms, the single enantiomers and diastereoisomers of the compounds of formula (I), as well as mixtures thereof.

The present invention also concerns the non-toxic salts of the compounds of formula (I) with acids acceptable for pharmaceutical and veterinary use such as those obtained by addition of inorganic acids such as hydrochloric, hydrobromic, sulfuric, phosphoric, pyrophosphoric acid, and/or of organic acids such as acetic, propionic, citric, benzoic, lactic, maleic, fumaric, succinic, tartaric, glutamic, aspartic, gluconic, ascorbic acids and the like.

DETAILED DESCRIPTION OF THE INVENTION

Figure 1:
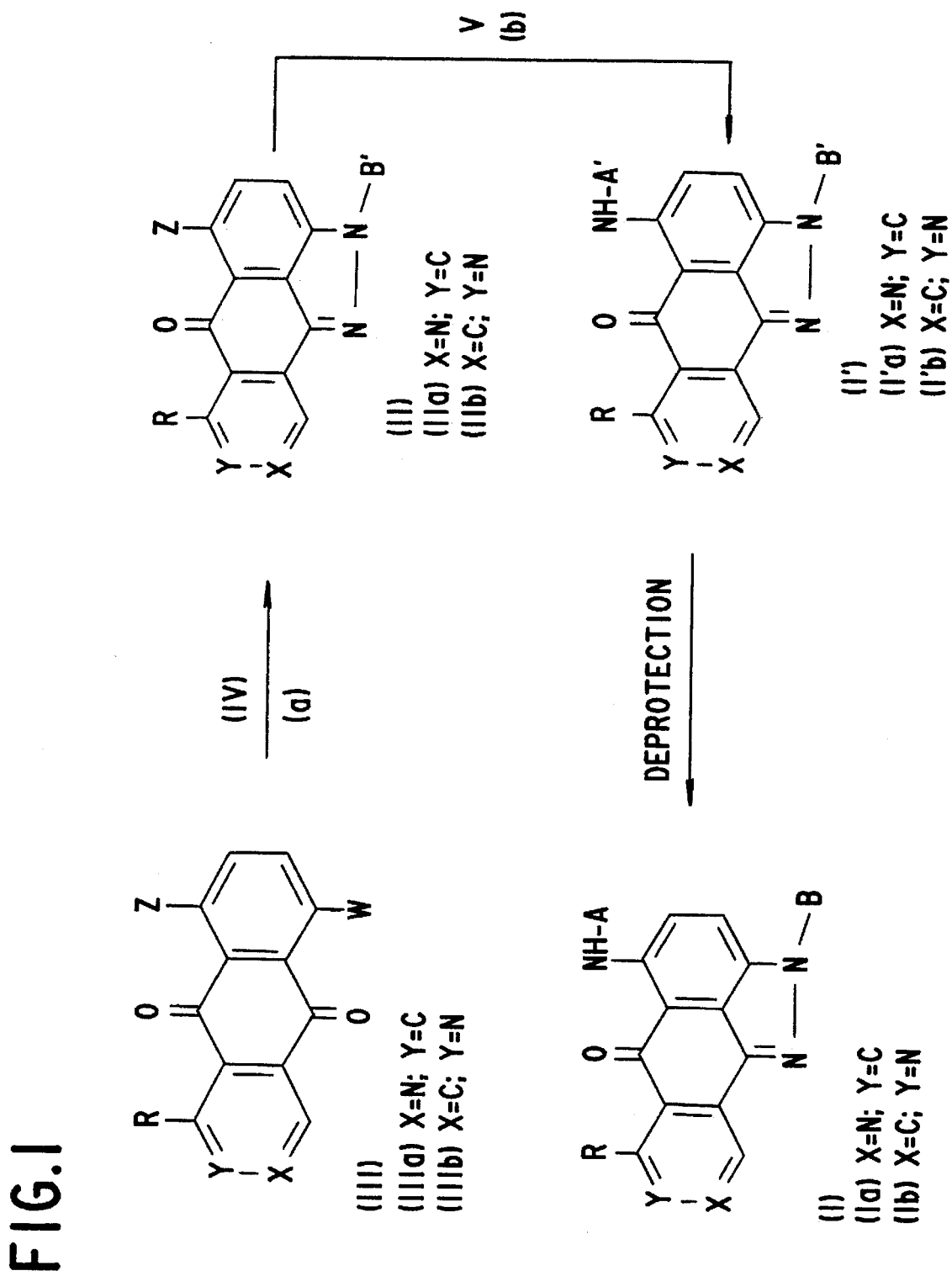
FIG. 1 depicts a method for the production of the compounds of Formula I according to the invention from compounds of Formula III.
Figure 2:
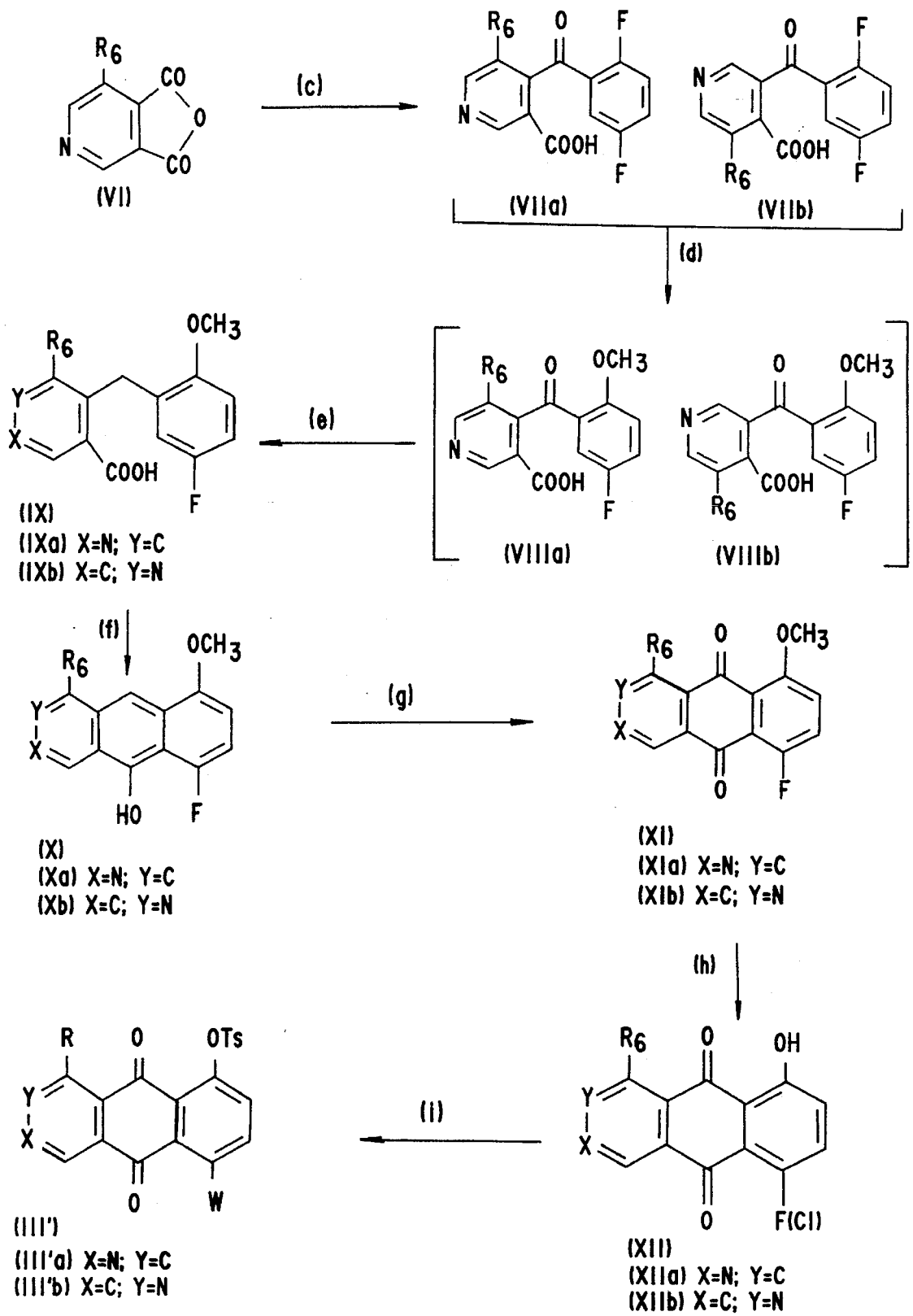
FIG. 2 depicts a method for the production of the preferred starting materials of Formula III'.
Figure 3:
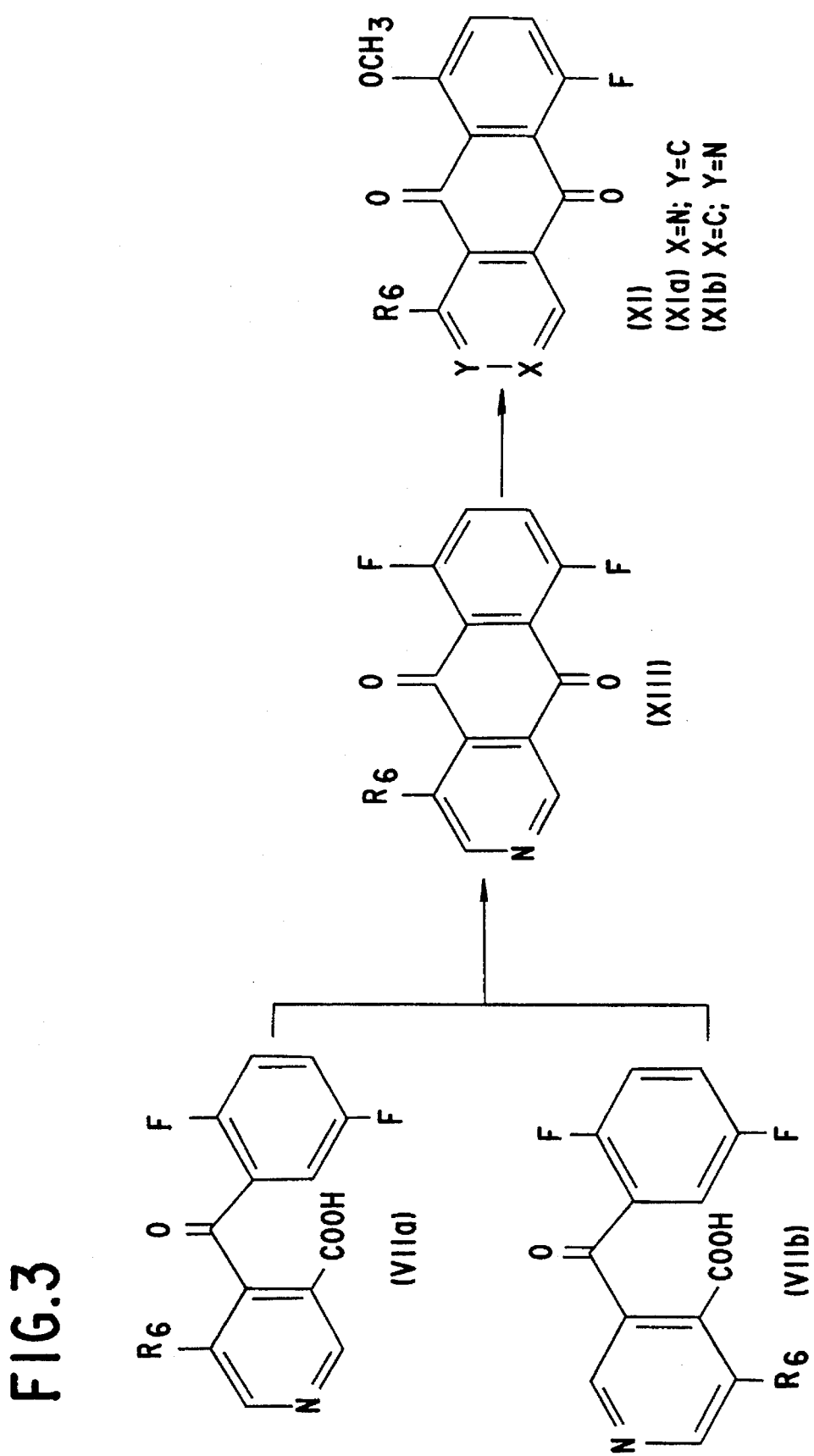
FIG. 3 depicts an alternative method for the product of the intermediate compounds of Formula XI for the production of compounds of Formula III'.
Figure 4:
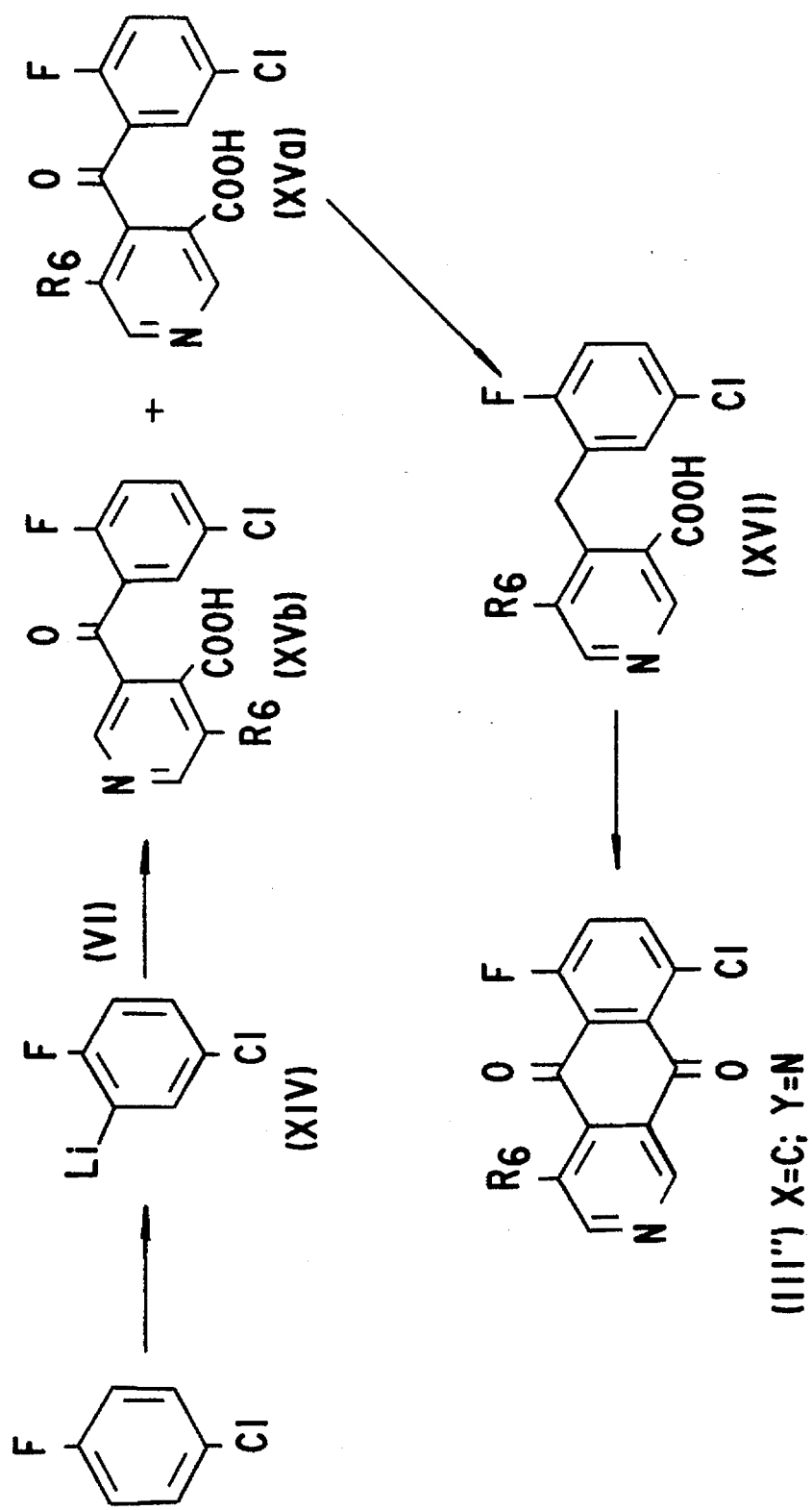
FIG. 4 depicts a method for the production of the preferred starting materials of Formula III".

In compounds (I) the term "phenyl" means phenyl rings which can optionally contain one or two substituents such as $C_1-C_4$ alkyl groups, $CF_3$, halogen atoms, nitro, amino, acetylamino, formylamino, dimethylamino, diethylamino, hydroxy, methoxy and ethoxy groups.

Preferred examples of $C_1-C_{10}$ alkyl groups are methyl, ethyl, n-propyl, sec-propyl, n-butyl, sec-butyl, tert-butyl, n-pentyl, n-hexyl.

Preferred examples of [phenylalkyl]are benzyl and 4-methoxy benzyl. When in compounds of formula (I) A or B are a $C_2-C_{10}$ alkyl interrupted by one or two oxygen atoms or by one —$NR_4$— group and optionally substituted by one or two hydroxy or —$NR_2R_3$ groups, at least two carbon atoms are preferably interposed, between said oxygen atoms and/or the —$NR_4$— and —$NR_2R_3$ groups.

When in compounds of formula (I), the —$NR_2R_3$ substituent is a 5- or 6-member aromatic or non-aromatic heterocyclic ring which may contain another heteroatom such as sulfur, oxygen and nitrogen, preferred examples of said heterocyclic rings are 1-imidazolyl, 1-pyrrolyl, 1-tetrahydropyrrolyl, 1-pyrazolyl, 4-morpholinyl, 1-piperidinyl, 1-piperazinyl, 1-(4-methyl)-piperazinyl, and 1-(4-benzyl)piperazinyl.

Preferred compounds of the invention are those of formula (I) where R is H and X and Y are as above defined.

Most preferred compounds are those of formula (I) where R is H, X and Y are as above defined, and A and B are independently selected from the group consisting of:

residue of formula —$(CH_2)_p$—$NH_2$ wherein p is the integer 2 or 3;

residue of formula —$(CH_2)p$—$NR_2R_3$ wherein p is as above defined and $R_2$ and $R_3$ are methyl;

residue of formula —$(CH_2)_p$—$NR_2R_3$ wherein p is as above defined and $R_2$ is hydrogen and $R_3$ is methyl;

residue of formula —$(CH_2)_p$—OH wherein p is as above defined;

residue of formula —$(CH_2)_p$—NH—$(CH_2)_q$—OH wherein p and q are independently an integer selected from the group consisting of 2 or 3;

Specific examples of the preferred compounds of this invention are reported in table 1 and have the following chemical names:

(1) 2-[2-[(2-hydroxyethyl)amino]ethyl]-5-[[2-[(2-hydroxyethyl)amino]ethyl]amino]isoquino[8,7,6-cd]indazole-6(2H)-one;

(2) 2-[2-[(2-hydroxyethyl)amino]ethyl]-5-[(3-aminopropyl)amino]isoquino[8,7,6-cd]indazole-6(2H)-one;

(3) 2-[2-[(2-hydroxyethyl)amino]ethyl]-5-[(2-aminoethyl)amino]isoquino[8,7,6-cd]indazole-6(2H)-one;

(4) 2-[2-[(2-hydroxyethyl)amino]ethyl]-5-[[2-(methylamino)ethyl]amino]isoquino[8,7,6-cd]indazole-6(2H)-one;

(5) 2-[2-[(2-hydroxyethyl)amino]ethyl]-5-[[2-(dimethylamino)ethyl]amino]isoquino[8,7,6-cd]indazole-6(2H)-one;

(6) 2-[2-[(2-hydroxyethyl)amino]ethyl]-5-[[2-[(2-hydroxyethyl)amino]ethyl]amino]isoquino[5,6,7-cd)indazole-6(2H)-one;

(7) 2-[2-[(2-hydroxyethyl)amino]ethyl]-5-[(3-aminopropyl)amino]isoquino[5,6,7-cd]indazole-6(2H)-one;

(8) 2-[2-[(2-hydroxyethyl)amino]ethyl]-5-[(2-aminoethyl)amino]isoquino[5,6,7-cd]indazole-6(2H)-one;

(9) 2-[2-[(2-hydroxyethyl)amino]ethyl]-5-[[2-(methylamino)ethyl]amino]isoquino[5,6,7-cd]indazole-6(2H)-one;

(10) 2-[2-[(2-hydroxyethyl)amino]ethyl]-5-[[2-(dimethylamino)ethyl]amino]isoquino[5,6,7-cd]indazole-6(2H)-one;

(11) 5-[[2-[(2-hydroxyethyl)amino]ethyl]amino]-2-[2-(dimethylamino)ethyl]isoquino[8,7,6-cd]indazole-6-(2H)-one;

(12) 5-[(3-aminopropyl)amino]-2-[2-(dimethylamino)ethyl]isoquino[8,7,6-cd]indazole-6(2H)-one;

(13) 5-[(2-aminoethyl)amino]-[2-[2-(dimethylamino)ethyl]isoquino[8,7,6-cd]indazole-6(2H)-one;

(14) 5-[[2-(methylamino)ethyl]amino]-2-[2-(dimethylamino)ethyl]isoquino[8,7,6-cd]indazole-6(2H)-one;

(15) 5-[[2-(dimethylamino)ethyl]amino]-2-[2-(dimethylamino)ethyl]isoquino[8,7,6-cd]indazole-6(2H)-one;

(16) 5-[[2-[(2-hydroxyethyl)amino]ethyl]amino]-2-[2-(dimethylamino)ethyl]isoquino[5,6,7-cd]indazole-6(2H)-one;

(17) 5-[(3-aminopropyl)amino]-2-[2-(dimethylamino)ethyl]isoquino[5,6,7-cd]indazole-6(2H)-one;

(18) 5-[(2-aminoethyl)amino]-[2-(dimethylamino)ethyl]isoquino[5,6,7-cd]indazole-6(2H)-one;

(19) 5-[[2-(methylamino)ethyl]amino]-2-[2-(dimethylamino)ethyl]isoquino[5,6,7-cd]indazole-6(2H)-one;

(20) 5-[[2-(dimethylamino)ethyl]amino]-2-[2-(dimethylamino)ethyl]isoquino[5,6,7-cd]indazole-6(2H)-one;

(21) 2-[2-aminoethyl]-5-[[2-[(2-hydroxyethyl)amino]ethyl]amino]isoquino[8,7,6-cd]indazole-6(2H)-one;

(22) 2-[2-aminoethyl]-5-[(3-aminopropyl)amino]isoquino[8,7,6-cd]indazole-6(2H)-one;

(23) 2-[2-aminoethyl]-5-[(2-aminoethyl)amino]isoquino[8,7,6-cd]indazole-6(2H)-one;

(24) 2-[2-aminoethyl]-5-[[2-(methylamino)ethyl]amino]isoquino[8,7,6-cd]indazole-6(2H)-one;

(25) 2-[2-aminoethyl]-5-[[2-(dimethylamino)ethyl]amino]isoquino[8,7,6-cd]indazole-6(2H)-one;

(26) 2-[3-aminopropyl)-5-[[2-[(2-hydroxyethyl)amino]ethyl]amino]isoquino[8,7,6-cd]indazole-6(2H)-one;

(27) 2-[3-aminopropyl]-5-[(3-aminopropyl)amino]isoquino[8,7,6-cd]indazole-6(2H)-one;

(28) 2-[3-aminopropyl]-5-[(2-amino)ethyl)amino]isoquino[8,7,6-cd]indazole-6(2H)-one;

(29) 2-[3-aminopropyl]-5-[[2-(methylamino)ethyl]amino]isoquino[8,7,6-cd]indazole-6(2H)-one;

(30) 2-[3-aminopropyl]-5-[[2-(dimethylamino)ethyl]amino]isoquino[8,7,6-cd]indazole-6(2H)-one;

(31) 5-[[2-[(2-hydroxyethyl)amino]ethyl]amino]-2-[3-aminopropyl]isoquino[5,6,7-cd]indazole-6(2H)-one;
(32) 5-[[2-[(2-hydroxyethyl)amino]ethyl]amino]-2-[2-aminoethyl]isoquino[5,6,7-cd]indazole-6(2H)-one;
(33) 2-[(2-methylamino)ethyl]-5-[[2-[(2-hydroxyethyl)amino]ethyl]amino]isoquino[8,7,6-cd]indazole-6(2H)-one
(34) 2-[(2-methylamino)ethyl]-5-[(3-aminopropyl)amino]isoquino[8,7,6-cd]indazole-6(2H)-one;
(35) 2-[(2-methylamino)ethyl]-5-[(2-aminoethyl)amino]isoquino[8,7,6-cd]indazole-6(2H)-one;
(36) 2-[(2-methylamino)ethyl]-5-[[2-(methylamino)ethyl]amino]isoquino[8,7,6-cd]indazole-6(2H)-one;
(37) 2-[(2-methylamino)]ethyl]-5-[[2-(dimethylamino)ethyl]amino]isoquino[8,7,6-cd]indazole-6(2H)-one;
(38) 2-[(2-methylamino)ethyl]-5-[[2-[(2-hydroxyethyl)amino]ethyl]amino]isoquino[5,6,7-cd]indazole-6(2H)-one;
(39) 2-[(2-methylamino)ethyl]-5-[(3-aminopropyl)amino]isoquino[5,6,7-cd]indazole-6(2H)-one;
(40) 2-[(2-methylamino)ethyl]-5-[(2-aminoethyl)amino]isoquino[5,6,7-cd]indazole-6(2H)-one;
(41) 2-[(2-methylamino)ethyl]-5-[[2-(methylamino)ethyl]amino]isoquino[5,6,7-cd]indazole-6(2H)-one;
(42) 2-[(2-methylamino)ethyl]-5-[[2-(dimethylamino)ethyl]amino]isoquino[5,6,7-cd]indazole-6(2H)-one;
(43) 2-methyl-5-[[2-(dimethylamino)ethyl]amino]isoquino[5,6,7-cd]indazole-6(2H)-one;
(44) 2-methyl-5-[[2-(dimethylamino)ethyl]amino]isoquino[5,6,7-cd]indazole-6(2H)-one.

TABLE 1

| No. | Y | X | R | A | B |
|-----|---|---|---|---|---|
| 1 | C | N | H | $CH_2CH_2NHCH_2CH_2OH$ | $CH_2CH_2NHCH_2CH_2OH$ |
| 2 | C | N | H | $CH_2CH_2CH_2NH_2$ | " |
| 3 | C | N | H | $CH_2CH_2NH_2$ | " |
| 4 | C | N | H | $CH_2CH_2NHCH_3$ | " |
| 5 | C | N | H | $CH_2CH_2N(CH_3)_2$ | " |
| 6 | N | C | H | $CH_2CH_2NHCH_2CH_2OH$ | $CH_2CH_2NHCH_2CH_2OH$ |
| 7 | N | C | H | $CH_2CH_2CH_2NH_2$ | " |
| 8 | N | C | H | $CH_2CH_2NH_2$ | " |
| 9 | N | C | H | $CH_2CH_2NHCH_3$ | " |
| 10 | N | C | H | $CH_2CH_2N(CH_3)_2$ | " |
| 11 | C | N | H | $CH_2CH_2NHCH_2CH_2OH$ | $CH_2CH_2N(CH_3)_2$ |
| 12 | C | N | H | $CH_2CH_2CH_2NH_2$ | " |
| 13 | C | N | H | $CH_2CH_2NH_2$ | " |
| 14 | C | N | H | $CH_2CH_2NHCH_3$ | " |
| 15 | C | N | H | $CH_2CH_2N(CH_3)_2$ | " |
| 16 | N | C | H | $CH_2CH_2NHCH_2CH_2OH$ | $CH_2CH_2N(CH_3)_2$ |
| 17 | N | C | H | $CH_2CH_2CH_2NH_2$ | " |
| 18 | N | C | H | $CH_2CH_2NH_2$ | " |
| 19 | N | C | H | $CH_2CH_2NHCH_3$ | " |
| 20 | N | C | H | $CH_2CH_2N(CH_3)_2$ | " |
| 21 | C | N | H | $CH_2CH_2NHCH_2CH_2OH$ | $CH_2CH_2NH_2$ |
| 22 | C | N | H | $CH_2CH_2CH_2NH_2$ | " |
| 23 | C | N | H | $CH_2CH_2NH_2$ | " |
| 24 | C | N | H | $CH_2CH_2NHCH_3$ | " |
| 25 | C | N | H | $CH_2CH_2N(CH_3)_2$ | " |
| 26 | C | N | H | $CH_2CH_2NHCH_2CH_2OH$ | $CH_2CH_2CH_2NH_2$ |
| 27 | C | N | H | $CH_2CH_2NH_2$ | " |
| 29 | C | N | H | $CH_2CH_2NHCH_3$ | " |
| 30 | C | N | N | $CH_2CH_2N(CH_3)_2$ | " |
| 31 | N | C | H | $CH_2CH_2NHCH_2CH_2OH$ | $CH_2CH_2CH_2NH_2$ |
| 32 | N | C | H | $CH_2CH_2NHCH_2CH_2OH$ | $CH_2CH_2NH_2$ |
| 33 | C | N | H | $CH_2CH_2NHCH_2CH_2OH$ | $CH_2CH_2NHCH_3$ |
| 34 | C | N | H | $CH_2CH_2CH_2NH_2$ | " |
| 35 | C | N | H | $CH_2CH_2NH_2$ | " |
| 36 | C | N | H | $CH_2CH_2NHCH_3$ | " |
| 37 | C | N | H | $CH_2CH_2N(CH_3)_2$ | " |
| 38 | N | C | H | $CH_2CH_2NHCH_2CH_2OH$ | $CH_2CH_2NHCH_3$ |
| 39 | N | C | H | $CH_2CH_2CH_2NH_2$ | " |
| 40 | N | C | H | $CH_2CH_2NH_2$ | " |
| 41 | N | C | H | $CH_2CH_2NHCH_3$ | " |
| 42 | N | C | H | $CH_2CH_2N(CH_3)_2$ | " |
| 43 | C | N | H | $CH_2CH_2N(CH_3)_2$ | $CH_3$ |
| 44 | N | C | H | $CH_2CH_2N(CH_3)_2$ | $CH_3$ |

The compounds of this invention can be prepared by the process depicted in scheme 1 and involving the reaction (reaction a) of a compound of formula (III):

[Structure of formula (III) with R, O, Z, W, O, X, Y positions]

(IIIa)  X = N, Y = C
(IIIb)  X = C, Y = N wherein Z is OTs (OTs being the p-toluenelsulfonyloxy group) or Cl and W is F or Cl, with the proviso that Z and W can not simultaneously be Cl, with a hydrazine of formula (IV):

$$H_2N-NH-B'$$ (IV)

where B' has the same meanings as B is defined in formula (I), or B' is a group that can be converted into B by removal of protective groups for the primary or secondary amines optionally present in B', to give a compound of formula (II):

[Structure of formula (II)]

(IIa)  X = N, Y = C
(IIb)  X = C, Y = N which then is reacted (reaction b) with a compound of formula (V):

$$H_2N-A'$$ (V)

where A' has the same meanings as A is defined in formula (I), or A' is a group that can be converted into A by removal of protective groups for the primary or secondary amines optionally present in A', to give the compounds of formula (I'):

[Structure of formula (I')]

When A' and/or B' are different from A and/or B, compounds of formula (I') are converted to compounds of formula (I) by removal of the protective groups for the primary and/or secondary amines optionally present in A' and/or B'.

When, if desired, the process depicted in scheme 1 is performed by reacting compounds of formula (IIIa), then the compounds of the invention of formula (Ia) can be obtained where X represents an atom of nitrogen and Y represents a carbon atom. Alternatively, if desired, by reacting compounds of formula (IIIb), the compounds of formula (Ib) can be obtained.

Protective groups for the primary and/or secondary amines optionally present in A' and/or B' which can advantageously be used for the preparation of compounds of formula (I) are represented by $(C_1-C_3)$acyl-derivatives (preferably acetyl-derivatives), $(C_1-C_4)$ alkoxycarbonyl-derivatives (preferably tert-butoxycarbonyl-derivatives) and by $(C_7-C_{10})$aralkyloxycarbonylderivatives (preferably benzyloxycarbonyl-derivatives).

In a preferred embodiment of this invention, compounds of formula (I) are prepared by reaction of a compound of formula (III'):

[Structure of formula (III') with R, O, OTs, W positions]

with a hydrazine of formula (IV) to give a compound of formula (II'):

[Structure of formula (II')]

Compounds of formula (II') are then reacted with a compound of formula (V) to give a compound of formula (I'), which step is followed by removal of the protective groups for the primary and secondary amines optionally present in A' and/or B', to give a compound of formula (I).

In another preferred embodiment of this invention compounds of formula (I) wherein X is C and Y is N are preferably prepared by reaction of a compound of formula (III"):

[Structure of formula (III") with R, O, F, Cl positions]

with a hydrazine of formula (IV) to give a compound of formula (II"):

[Structure of formula (II")]

Compounds of formula (II") are then reacted with a compound of formula (V) to give a compound of formula (I'), which step is followed by removal of the protective groups for the primary and secondary amines optionally present in A' and/or B', to give a compound of formula (I) wherein X is C and Y is N.

The reaction of compounds (III) with the hydrazines (IV) can be performed by heating compounds (III) with a stoichiometric amount of hydrazines (IV) or an excess of hydrazines (IV). The reaction is usually performed in an inert solvent such as methylene chloride, chloroform, 1,1,1-trichloroethane, dimethoxyethane, tetrahydrofuran, dimethylsulfoxide, dimethylformamide, pyridine, picoline, and mixtures thereof, or if it is desired, using compound (IV) itself as the solvent, optionally in the presence of an inorganic base such as an alkaline or alkaline-earth carbonate or hydrogen carbonate or an organic base such as a trialkylamine, at a temperature from 0° C. to the reflux temperature of the solvent.

Preferably the reaction is carried out in a solvent such as pyridine, tetrahydrofuran, dimethylsulfoxide, or N,N,N',N'-tetramethylethylenediamine, using from 2 to 10 equivalents of compound (IV) for 1 equivalent of compound (III), and working at a temperature ranging from 5° C. to 50° C.

When, in a particular embodiment of this invention, a compound of formula (III') is reacted with a hydrazine of formula (IV), the reaction is preferably performed with a molar ratio between compounds (III) and (IV) of 1:1.05 to 1:1.25 and by using tetrahydrofuran as solvent at a temperature ranging from room temperature to 50° C.

The reaction of the compounds of formula (II) with the compounds of formula (V) can be performed by heating compounds (II) with a stoichiometric amount of amine (V) or an excess of amine (V). The reaction is usually performed in an inert solvent such as methylene chloride, chloroform, 1,1,1-trichloroethane, dimethoxyethane, tetrahydrofuran, dimethylsulfoxide, dimethylformamide, pyridine, picoline, and mixtures thereof, or, if it is desired, using compound (V) itself as the solvent, optionally in the presence of an inorganic base such as an alkaline or alkaline-earth carbonate or hydrogen carbonate or an organic base such as a trialkylamine, at a temperature from 0° C. to the reflux temperature of the solvent.

Preferably the reaction is carried out in a solvent such as pyridine, chloroform, or dimethylsulfoxide, using from 2 to 10 equivalents of compound (V) for 1 equivalent of compound (II), and working at a temperature ranging from room temperature to 100° C.

When, in the compounds of formula (I'), A' and/or B' are different from A and/or B, the removal of the protective group for the primary and/or secondary amino functions is carried out following the procedures well known to those skilled in the art. Useful teachings can be found in Green, T. W., Wuts, P. G. M., "Protective Groups in Organic Synthesis", second Edition, John Wiley & Sons, 1991.

For example, the removal of the N-(tert-butoxycarbonyl) protective group can be performed by treatment of a compound of formula (I') with an excess of anhydrous hydrochloric acid in a solvent such as a ($C_1$–$C_4$) alkanol, dichloromethane, chloroform, or mixtures thereof, at a temperature of 0° C. to the reflux temperature of the solvent and for a time ranging from several minutes to a few hours. Preferably the reaction is performed in ethanol or in chloroform using from 10 to 20 molar equivalents of anhydrous hydrochloric acid at a temperature of from 20° C. to 50° C., and is generally complete in four hours.

The compounds of formula (IV) are known or they can be prepared according to known procedures, see for example, J. Med. Chem., 7, 493, (1964) and J. Het. Chem., 26, 85, (1989).

The compounds of formula (V) are known and commercially available, or they can be prepared according to known procedures. For example, the preparation of some N-(tert-butoxycarbonyl) alkanediamines useful for the preparation of some compounds of the present invention is described in Synth. Comm., 20, 2559, (1990) or in J. Med. Chem., 33, 97, (1990).

The compounds of formula (III) wherein Z=OTs [compounds III')] an be prepared by a multistep procedure, depicted in scheme 2, involving the following reactions:

(c) the Friedel and Craft acylation of 1,4-difluorobenzene with pyridine-3,4-dicarboxylic anhydrides (VI) where $R_6$ is hydrogen or a suitable protecting group of the hydroxy function such as methoxy or benzyloxy, in presence of $AlCl_3$ (110° C., 22 h) which leads to the regioisomeric keto-acids (VIIa) and (VIIb);

(d) reaction of the ketoacids (VIIa) and (VIIb) with sodium methoxide in methanol (8.5 h, reflux) leading to the regioisomeric methoxy-substituted ketoacids (VIIIa) and (VIIIb); compounds (VIIIa) and (VIIIb) where $R_6$ is hydrogen can be reacted as such in the following step; when $R_6$ is different from hydrogen, compound (VIIIa) is purified by crystallization and reacted as pure regioisomer;

(e) reduction of compounds (VIIIa) ($R_6$ different from hydrogen) with Zn/Cu couple in 75% aqueous formic acid (15' room temperature, then 80° C., 2 h) leading to (IX); when $R_6$ is hydrogen, the acids (IXa) and (IXb) can be separated by chromatography yielding the pure isolated regioisomers (IXa) and (IXb);

(f) cyclization of the appropriate acid (IX) by heating a suspension of the compound in polyphosphoric acid at 110°–120° C. for 2 h leading to the benzo[g]isoquinoline (X);

(g) oxidation of the compound (X) to the corresponding dione (XI) by cerium ammonium nitrate in a mixture of acetonitrile and water (60° C., 2 h);

(h) removal of the methoxy group of the dione (XI) by aluminum chloride in methylene chloride (room temperature 2 h, then reflux temperature 1.5 h) leading to compounds (XII) which correspond to a mixture of 9-fluoro-6-hydroxy and 9-chloro-6-hydroxy-5,10-diones (XII) due to partial substitution of the leaving fluoride by means of $AlCl_3$; and (i) the final functionalization of the free hydroxy group of (XII) by means of toluenesulfonyl chloride in pyridine at room temperature, leads to the desired compounds (III) wherein Z=OTs [compounds (III)]; when $R_6$ is a protective group of the hydroxy function, it can be removed according to methods well known to the expert in the art, thus leading to compound (III) where R is OH.

In a preferred embodiment of this invention, the preparation of intermediates (XI) is carried out by a multistep procedure depicted in scheme 3 and involving the following reactions:

cyclization of the mixture of the regioisomeric keto-acids (VIIa) and (VIIb) with 20% oleum at 130°–140° C. to give the 6,9-difluorobenzo[g]isoquinolines (XIII);

reaction of (XIII) with one equivalent of sodium methylate in a solvent such as methanol to give a mixture of intermediates (XI) which is separated into the single pure compounds (XIa) and (XIb) by recrystallization from a solvent and/or column chromatography. The pure intermediates (XIa) and (XIb) are then processed according to equation (h) and (i) of scheme 2 and then according to scheme 1 to give compounds (Ia) and (Ib), respectively.

In the preferred process of this invention which provides the compounds of formula (I) wherein X=C and Y=N, the 9-chloro-6-fluorobenzo[g]isoquinoline-5,10-diones of formula (III") are prepared by the multistep process depicted in scheme 4 and involving the following reactions:

lithiation of 1-chloro-4-fluorobenzene with an alkyllithium reagent such as sec-butyllithium in THF at −75° C. to give 1-lithio-5-chloro-2-fluorobenzene (XIV);

acylation of 1-lithio-5-chloro-2-fluorobenzene (XIV), generated in situ according to the above step, with pyridine-3,4-dicarboxylic anhydrides (VI) to give the mixture of keto-acids (XVa) and (XVb) which can be separated into the single pure compounds by recrystallization from a solvent or by sublimation;

reduction of the pure keto-acid (XVa) with Zn/Cu couple or Zn powder in 75% aqueous formic acid (15' at room temperature, then 80° C., 2 hrs) leading to (XVI);

oxidative cyclization of (XVI) with fuming sulfuric acid (20–30% $SO_3$, 10', 130° C.) to give the 9-chloro-6-fluorobenzo[g]isoquinoline-5,10-diones of formula (III").

Intermediates (III") are then processed according to scheme 1 to give the compounds of formula (I) wherein X=C and Y=N.

BIOLOGICAL ACTIVITY OF COMPOUNDS OF THE INVENTION

The evaluation of the biological activity for the compounds of this invention was performed in vitro and in vivo following the protocols developed by the U.S. National Cancer Institute.

The evaluation of the in vitro cytotoxic activity of the compounds of the invention was performed using a human colon adenocarcinoma cell line (Lovo) isolated from a metastatic nodule, and a subline expressing multidrug resistance. The subline is resistant to a number of antitumor agents, among which are doxorubicin, VP-16, and vincristine. This subline (named Lovo/DX) shows reduced accumulation of doxorubicin and overexpression of a protein (Grandi, M., Geroni, C., Giuliani, F. C., British J. Cancer, (1986), 54, 515). The compounds were tested according to the MTT assay (Mosman, T. "Rapid Colorimetric assay for cellular growth and survival: application to proliferation and cytotoxicity assay", J. Immunol. Methods, (1983), 65, 55–63; Green, L. M., "Rapid colorimetric assay for cell viability; application to the quantitation of cytotoxic and growth inhibitory lymphokines", J. Immunol. Methods, (1984), 70, 257–268) in comparison with mitoxantrone, and doxorubicin.

TABLE 2

| compound | $IC_{50}$ (µg/ml) LOVO | LOVO/DX | RI |
|---|---|---|---|
| [structure: 6-aza anthraquinone with 5-NH-CH₂CH₂-N(CH₃)₂ and 8-N-NH-CH₂CH₂-NH₂] | 0.3 | 5.0 | 16.7 |
| [structure: 6-aza anthraquinone with 5-NH-CH₂CH₂-NH₂ and 8-N-NH-CH₂CH₂-N(CH₃)₂] | 0.5 | 22.4 | 44.8 |
| [structure: 6-aza anthraquinone with 5-NH-CH₂CH₂-N(CH₃)₂ and 8-N-NH-CH₂CH₂-N(CH₃)₂] | 0.5 | 0.9 | 1.8 |
| MITOXANTRONE | 0.04 | 0.9 | 22.5 |
| DOXORUBICIN | 0.9 | 66.6 | 74 |

In general, representative compounds of this invention were more cytotoxic than doxorubicin and as cytotoxic as mitoxantrone in the Lovo cell line. When mitoxantrone was tested in the Lovo/DX cell line, a resistance index RI (defined a the ratio of the $IC_{50}$ for the resistant line cell to the $IC_{50}$ for the sensitive cell line) as high as 22.5 was found, showing that this subline does have an acquired resistance to mitoxantrone and ametantrone. On the other hand, some compounds of this invention, when tested in the same resistant subline, show no cross resistance with mitoxantrone and ametantrone as reported in Table 2. The in vitro evaluation of representative compounds of this invention suggests that representative compounds of this invention may be useful in order to overcome the multidrug resistance-mediated mechanism of tumor resistance.

Studies of the biological activity in vivo of representative compounds of the invention were performed using the P388 and L1210 murine leukemia models. P388 murine leukemia cells were intraperitoneally (ip) or intravenously (iv) injected in CD2F1 mice. Treatment was initiated approximately 24 hours after tumor transplantation and dosages of the drug were administered ip (P388 ip/ip) or iv (P388 iv/iv)

according to preestablished protocols, usually at 3-day (P388 iv/iv) or 4-day (P388 ip/ip) intervals. The studies were done over a 60-day period and the date of death for each animal was recorded. The % T/C was determined using the mean survival time (MST) for each group according to the formula % T/C=[(MST treated)/(MST control)]×100

Representative compounds of this invention were able to increase the survival time of treated animals significantly more than mitoxantrone, leading to higher T/C % values at well tolerated dosages. Moreover, the above representative compounds of the invention showed antileukemic activity over a wide range of well tolerated dosages, and, in particular, were active at dosages which were lower than the maximum tolerated dose, providing indication for more favorable therapeutic index in comparison to mitoxantrone.

The antitumor activity of representative compounds of this invention was evaluated also in the L1210 murine leukemia model.

L1210 leukemia cells were intraperitoneally (ip) or intravenously (iv) injected in CDF1 mice and treatment was initiated approximately 24 hours after tumor transplantation. Dosages of the drugs were administered ip (L1210 ip/ip) or iv (L1210 iv/iv) according to preestablished protocols, usually at 3-day (L1210 iv/iv) or 4-day (L1210 ip/ip) intervals. The studies were done over a 60-day period and the date of death for each animal was recorded. The % T/C was determined using the mean survival timed (MST) for each group according to the formula:

% T/C [(MST treated)/(MST control)]×100

Also in this further leukemia model, representative compounds of this invention showed activity superior to the clinically used antitumor drug mitoxantrone. Since representative compounds of this invention show good results against in vivo models of murine P388 and L1210 leukemias, which are considered to be predictive of antitumor activity in humans, the compounds disclosed herein are expected to be operative against human leukemias and solid tumors sensitive to treatment with antitumor antibiotics.

The compounds of the present invention may therefore be used as active ingredients of therapeutic compositions to induce regression and/or palliation of cancers in mammals when administered in amounts ranging from about 1 mg to about 0.4 g per kilogram of body weight. A preferred dosage regimen would be from about 1 mg to about 50 mg per kilogram of body weight per day. Unit dosage may be employed so that from about 70 mg to about 3.5 g of the active compound for a subject of about 70 kg of body weight are administered in a 24-hour period. The dosage may be adjusted to be compatible to other treatment regimens, such as radiation therapy.

The pharmaceutical composition may be in the form of tablets, capsules, gel capsules, suppositories, lyophilized powders and solutions for intravenous administration. The invention is illustrated by the following non-limiting examples, and variations which are readily apparent to those skilled in the art.

SYNTHESIS OF COMPOUNDS OF THE INVENTION

Preparative Example 1

Pyridine-3,4-dicarboxylic Acid Anhydride

A mixture of pyridine 3,4-dicarboxylic acid (15.0 g) and acetic anhydride (30 mL) is refluxed for two hours. The excess acetic anhydride is removed by distillation and the anhydride is collected and purified by sublimation (123° C. at 3 mm Hg) to yield pyridine 3,4-dicarboxylic acid anhydride as a white solid (10.1 g).

m.p.: 74°–76° C.

$^1$H-NMR (CDCl$_3$): 7.94 (d, 1H); 9.24 (d, 1H); 9.39 (s, 1H).

Preparative Example 2

4-(2,5-difluorobenzoyl)nicotinic Acid and 3-(2,5-difluorobenzoyl)isonicotinic Acid A mixture of pyridine 3,4-dicarboxylic acid anhydride (5.0 g) and aluminum chloride (17.5 g) in 1,4-difluorobenzene (65 mL) is heated in an oil bath at 110° C. for 22 hours. The excess 1,4-difluorobenzene is recovered by distillation. The residue is cooled in an ice-bath and quenched with ice-water (75 mL) and concentrated hydrochloric acid (6.3 mL). The precipitated solid is filtered and dried to yield an approximately 4/1 mixture of 4-(2,5-difluorobenzoyl)nicotinic acid and 3-(2,5-difluorobenzoyl) isonicotinic acid respectively, as a white powder (7.7 g) which can be recrystallized from acetonitrile and water.

m.p.: 214°–217° C.

$^1$H-NMR (DMSO-d$_6$): 7.4 (m); 7.5 (m); 7.90 (m); 8.80 (d); 8.90 (d); 9.15 (s).

Recrystallization of this material (15.97 g) from absolute ethanol (360 mL) yields almost pure 3-(2,5-difluorobenzoyl) isonicotinic acid (1.146 g).

Preparative Example 3

4-(2-methoxy-5-fluorobenzoyl)nicotinic Acid and 3-(2-methoxy-5-fluorobenzoyl)isonicotinic Acid The mixture of 4-(2,5-difluorobenzoyl)nicotinic acid and 3-(2,5-difluorobenzoyl)isonicotinic acid of Preparative Example 2 (14.1 g) is added to a solution of sodium methylate, prepared by portionwise addition of sodium (6.8 g) to dry methanol (140 mL). The reaction mixture is allowed to react at the reflux temperature for 8.5 hours and at room temperature overnight. The reaction mixture is concentrated to about one third of its volume, water (100 mL) is added and the remaining methanol is removed by distillation. Concentrated HCl (25 mL) is slowly added to the residue while cooling at 10° C. and the obtained precipitate is recovered by suction and washed with 0.1N HCl, to give an approximately 4:1 mixture of 4-(2-methoxy-5-fluorobenzoyl) nicotinic acid and 3-(2-methoxy-5-fluorobenzoyl)isonicotinic acid (11.31 g).

m.p.: >230° C.

$^1$H-NMR (DMSO-d$_6$): 3.40 (s); 3.45 (s); 7.15 (m); 7.37 (d); 7.42–7.63 (m); 7.26 (d); 8.60 (s); 8.83 (d); 9.07 (s), 13.55 (br.s).

Preparative Example 4

4-(2-methoxy-5-fluorobenzyl)nicotinic Acid (and 3-(2-methoxy-5-fluorobenzyl)isonicotinic Acid)

Zinc-copper couple (L. F. Fieser and M. Fieser, Reagents for Organic Synthesis, Vol. 1, page 1292) (1.5 g) is added to a stirred suspension of the mixture of 4-(2-methoxy-5-fluorobenzoyl)nicotinic acid and 3-(2-methoxy-5-fluorobenzoyl)isonicotinic acid of Preparative Example 3 (1.222 g) in formic acid (15 mL) and water (5 mL). After 15 minutes at room temperature the reaction mixture is heated for two hours in a oil bath held at 80° C. After cooling to room temperature the reaction mixture is filtered through a sintered glass filter and the solids are thoroughly washed with 75% aqueous formic acid (10 mL) and then with ethyl acetate (10 mL). The combined filtrates are concentrated to about 5 mL, treated with 0.5N HCl (15 mL) and extracted with ethyl acetate (3×20 mL); finally they are saturated with sodium chloride and further extracted with ethyl acetate/1,2-dimethoxyethane 3/1 (2×20 mL). The combined organic phases are dried over anhydrous sodium sulphate and the solvent removed under reduced pressure to give a yellowish residue. Subjecting this material to silica-gel column chromatography (eluant: ethyl acetate/methanol/acetic acid from 96/4/0 to 90/10/1 v/v/v) 4-(2-methoxy-5-fluorobenzyl)nicotinic acid (0.805 g) is obtained as a yellowish white solid.

m.p.: >220° C.

$^1$H-NMR (DMSO-$d_6$): 3.70 (s, 3H); 4.33 (s, 2H); 6.91–7.12 (m, 3H); 7.21 (d, 1H); 8.61 (d, 1H); 8.97 (s, 1H). From the above column-chromatography some 3-(2-methoxy-5-fluorobenzyl)isonicotinic acid may also be recovered.

Preparative Example 5

9-fluoro-10-hydroxy-6-methoxybenzo[g]isoquinoline

A mixture of 4-(2-methoxy-5-fluorobenzyl) nicotinic acid (0.63 g) and polyphosphoric acid (15 g) is heated at 110°–120° C. for two hours under stirring. The heating is removed and water (50 mL) is added to the reaction mixture while it is still warm (60° C.). The mixture is cooled to 0° C., neutralized with 20% sodium hydroxide and allowed to stir at room temperature for 1.5 hours; finally it is extracted with 4% methanol in chloroform (4×75 mL). The combined organic phases are washed with brine, dried over anhydrous sodium sulphate and the solvents removed under reduced pressure to give 9-fluoro-10-hydroxy-6-methoxybenzo[g]isoquinoline (0.40 g) as a purple-red solid.

m.p.: >210° C. (from ethanol).

$^1$H-NMR (DMSO-$d_6$): 3.87 (s, 3H); 6.70–6.83 (m, 2H); 6.92–7.00 (m, 1H); 7.30 (d, 1H); 7.50 (d, 1H); 8.75 (s, 1H); 12.30 (br.s, 1H).

UV (ethanol): lambda max. (nm) (E $_{1\%}$) (cm): 539 (204); 398 (513); 378 (452); 266 (1232).

IR (KBr): 729, 1245, 1499, 1528, 1620, 1644, and 2838 cm$^{-1}$.

Preparative Example 6

9-fluoro-6-methoxybenzo[g]isoquinoline-5,10-dione

A solution of cerium ammonium nitrate (CAN; 13.70 g) in water (50 mL) is added during twenty minutes to a stirred Suspension of 9-fluoro-10-hydroxy-6-methoxybenzo[g]isoquinoline (1.22 g) in acetonitrile (150 mL). At the end of the addition the obtained suspension is heated at 60° C. for two hours to give a clear, dark solution which is cooled to room temperature and diluted with water (100 mL). Following removal of acetonitrile by distillation at reduced pressure the aqueous phase is saturated with sodium chloride and extracted with methylene chloride (3×150 mL). The combined organic solutions are dried over anhydrous sodium sulphate and the solvent is removed at reduced pressure. The obtained residue is purified by silica-gel column chromatography (eluant: methylene chloride/ethyl acetate from 85/15 to 75/25 v/v) to give 9-fluoro-6-methoxybenzo[g]isoquinoline5,10-dione as a brown-yellow solid (0.48 g).

m.p.: >220° C.

$^1$H-NMR (CDCl$_3$): 4.05 (s, 3H); 7.38 (dd, J=3.39, 9.39 Hz, 1H); 7.55 (dd, J=10.37, 9.39 Hz, 1H); 8.00 (dd, J=5.09, 0.78 Hz, 1H); 9.07 (d, J=5.09 Hz, 1H); 9.45 (d, J=0, 78 Hz, 1H).

Preparative Example 7

6,9-difluorobenzo[g]isoquinoline-5,10-dione

A solution of the mixture of 4-(2,5-difluorobenzoyl)nicotinic acid and 3-(2,5-difluorobenzoyl)isonicotinic acid of Preparative Example 2 (61.07 g) in 20% oleum (100 mL) is heated at 140° C. while 20% oleum is added in four portions (13.2 mL each) at 20 min-intervals. After the fourth addition the mixture is heated for 20 min, then it is cooled to room temperature and quenched with a mixture of ice (1,500 g), water (1,500 mL) and 35% NaOH (350 mL). The mixture is extracted four times with methylene chloride (1×1,000 mL followed by 3×500 mL). The combined organic solutions are washed with water (2×1,000 mL), dried (Na$_2$SO$_4$) and the solvent removed by roto-evaporation. The dark-red solid obtained (56.0 g) is dissolved in boiling THF (840 mL) and decolorizing charcoal (8.40 g) is added. After 30 min the mixture is filtered while hot and the filtrate concentrated to 200 mL. The precipitate obtained is collected by suction filtration to give 6,9-difluorobenzo[g]isoquinoline-5,10-dione (43.00 g).

m.p.: 201°–203° C.

Concentration of the mother liquor to 70 mL yields a second crop of product (3.35 g), m.p. 200°–202° C.

Preparative Example 8

9-fluoro-6-methoxybenzo[g]isoquinoline-5,10-dione
and
6-fluoro-9-methoxybenzo[g]isoquinoline-5,10-dione A solution of sodium methylate is prepared under a nitrogen atmosphere in a dropping addition funnel from dry methanol (97.6 mL) and sodium (2.024 g) portionwise added. When all the sodium disappears the solution is dropped during 2 h, 35 min to a stirred solution of 6,9-difluorobenzo[g]isoquinoline-5,10-dione of Preparative Example 7 (19.615 g) in dry THF (883 mL) at 20° C. At the end of the addition the solution is concentrated to half its volume by roto-evaporation, then it is cooled to 18° C. for 30 min. The solid which separates is recovered by suction filtration and washed with THF (100 mL); then it is suspended in water (80 mL) under stirring overnight and filtered again to give the solid A (7.4 g).

The mother THF solution is concentrated to dryness. The obtained solid is suspended in water (78 mL) under stirring for 1 hour and filtered to give the solid B (12.9 g).

The solid A (9.30 g) in methylene chloride (45 mL) is heated to reflux for 30 min. After cooling to room temperature the solid is recovered by suction filtration, washed with methylene chloride (5×3 mL) and dried under vacuum at 40° C. to give 6-methoxy-9-fluorobenzo[g]isoquinoline-5,10-dione (8.65 g) as a pure compound.

m.p.: 248°–250° C.

$^1$H-NMR (CDCl$_3$): 4.05 (s, 3H); 7.40 (dd (J=9.39, 3.91 Hz) 1H); 7.55 (dd, J=10.37, 9.39 Hz, 1H); 8.00 (dd, J=5.09, 0.78 Hz, 1H); 9.05 (d, J=5.09 Hz, 1H); 9.48 (d, J=0.78 Hz, 1H).

The solid B (14.0 g) is dissolved in methylene chloride (140 mL) and the insoluble portion is removed by filtration. The methylene chloride solution is applied on a silica gel (630 g) column chromatography, which is eluted at ambient pressure with methylene chloride. When the yellow chromatographic bands appear well separated the column is eluted with mixtures of methylene chloride/ethyl acetate from 10/1 to 8/2, to 1/1 to give a 94/6 mixture (HPLC evaluation) of 9-methoxy-6-fluorobenzo[g]isoquinoline-5,10-dione and 6-methoxy-9-fluorobenzo[g]isoquinoline-5,10-dione respectively (6.50 g).

m.p.: 168°–170° C.

Preparative Example 9 a)
9-fluoro-6-hydroxybenzo[g]isoquinoline-5,10-dione and
9-chloro-6-hydroxybenzo[g]isoquinoline-5,10-dione
(1/1 Mixture: Small Scale Reaction)

A mixture of 9-fluoro-6-methoxybenzo[g]isoquinoline-5,10-dione (0.072 g) and aluminum trichloride (0.112 g) in dry methylene chloride (40 mL) is stirred at room temperature for 4 hours under a nitrogen atmosphere. An additional portion of aluminum chloride (0.190 g) is added and the mixture is allowed to react at reflux for 1.5 hrs and at room temperature overnight. Following addition of brine (15 mL) the aqueous phase is separated and extracted with methylene chloride (3×5 mL). The combined organic solutions are dried over anhydrous sodium sulphate and the solvent is removed by distillation at reduced pressure to give an approximately 1:1 mixture (0.070 g) of 9-fluoro-6-hydroxybenzo[g]isoquinoline-5,10-dione (slower moving yellow spot on silica gel TLC plate, eluant methylene chloride/ethyl acetate 70/30) and 9-chloro-6-hydroxybenzo [g]isoquinoline-5,10-dione (faster moving yellow spot on the above chromatographic system) which is used without further purification for the next step.

9-fluoro-6-hydroxybenzo[g]isoquinoline-5,10-dione has the following $^1$H-NMR spectrum (CDCl$_3$): 7.38 (dd, 1H); 7.53 (dd, 1H); 8.09 (dd, 1H); 9.15 (d, 1H); 9.57 (d, 1H); 12.56 (s, 1H).

9-chloro-6-hydroxybenzo[g]isoquinoline-5,10-dione has the following $^1$H-NMR spectrum (CDCl$_3$): 7.91 (d, 1H); 7.75 (d, 1H); 8.07 (dd, 1H); 9.13 (d, 1H); 9.58 (d, 1H); 12.95 (s, 1H).

b)
9-fluoro-6-hydroxybenzo[g]isoquinoline-5,10-dione and
9-chloro-6-hydroxybenzo[g]isoquinoline-5,10-dione(9/1
Mixture: Multigram Preparation)

Aluminum chloride (19.05 g) is added in one portion to a stirred refluxing solution of 6-methoxy-9-fluorobenzo[g]isoquinoline-5,10-dione (7.20 g) in methylene chloride (432 mL). After refluxing for 4 hours the reaction mixture is cooled and poured in water (1,300 mL). Methylene chloride (200 mL) is added and after stirring for 10 min the organic phase is separated. The aqueous solution is saturated with NaCl and further extracted with methylene chloride (3×400 mL). The combined organic solutions are washed with brine (1,000 mL), dried and the solvent removed by roto-evaporation. The brown solid obtained (6.5 g) is recrystallized from ethyl acetate/n-hexane 1/1 (65 mL) to yield a 9/1 mixture ($^1$H-NMR evaluation) of 9-fluoro-6-hydroxybenzo[g]isoquinoline-5,10-dione and 9-chloro-6-hydroxybenzo[g]isoquinoline-5,10-dione respectively (6.00 g).

m.p.: partial melting at 179°–181° C.; complete melting at 193°–195° C.

Preparative Example 10 a)
9-fluoro-6-(p-toluenesulfonyloxy)benzo[g]isoquinoline-5,10-dione and 9-chloro-6-(p-toluenesulfonyloxy) benzo[g]isoquinoline-5,10-dione (1/1 Mixture; Small Scale Preparation)

The 1:1 mixture of 9-fluoro-6-hydroxybenzo[g]isoquinoline-5,10-dione and 9-chloro-6-hydroxybenzo[g]isoquinoline-5,10-dione, of Preparative Example 9a, (0.060 g) is dissolved in dry pyridine (2 mL) and p-toluenesulfonyl chloride (0.095 g) is added. After stirring at room temperature for one hour, triethylamine (0.25 mL) is added and stirring is continued for one additional hour. The reaction mixture is concentrated almost to dryness and partitioned between 1N HCl (4 mL)-20% ammonium sulfate (6 mL) and ethyl acetate (10 mL). The aqueous phase is separated, extracted with ethyl acetate (3×5 mL) and discarded. The combined organic solutions are dried over anhydrous sodium sulphate and concentrated to dryness to give an approximately 1:1 mixture (0.095 g) of 9-fluoro-6-(p-toluenesulfonyloxy)benzo[g]isoquinoline-5,10-dione and 9-chloro-6-(p-toluenesulfonyloxy) benzo[g]isoquinoline-5,10-dione which is used without further purification for the next step.

The pure single compounds can be obtained by silica-gel column chromatography of this mixture (eluant:methylene chloride/n-hexane/ethyl acetate from 50/45/5 to 50/40/10 v/v/v) and they have the following analytical data:

9-fluoro-6-(p-toluenesulfonyloxy)benzo[g]iso-quinoline-5,10-dione: m.p. 173°–174° C.

$^1$H-NMR (CDCl$_3$): 2.45 (s, 3H), 7.35 (d, 2H); 7.50–7.57 (m, 2H); 7.82–7.94 (m, 3H); 9.08 (d, 1H); 9.48 (s, 1H).

9-chloro-6-(p-toluenesulfonyloxy)benzo[g]isoquinoline-5,10-dione
m.p.: 180°–181° C.

$^1$H-NMR (CDCl$_3$): 2.45 (s, 3H); 7.35 (d, 2H); 7.47 (d, 1H); 7.78–7.91 (m, 4H), 9.07 (d, 1H); 9.48 (s, 1H).

b)
9-fluoro-6-(p-toluenesulfonyloxy)benzo[g]isoquinoline-5,10-dione and
9-chloro-6-(p-toluenesulfonyloxy)benzo[g]isoquinoline-5,10-dione (9/1 Mixture; Multigram Preparation)

Triethylamine (8.20 mL) is added to a stirred suspension of the 9/1 mixture of 9-fluoro-6-hydroxybenzo[g]isoquinoline-5,10-dione and 9-chloro-6-hydroxybenzo[g]isoquinoline-5,10-dione respectively of Preparative Example 9b (5.53 g) and p-toluenesulfonylchloride (8.47 mL) in methylene chloride (166 mL). The reddish-violet solution obtained is left at room temperature under a nitrogen atmosphere for 1 hour and then it is poured into water (500 mL). The organic phase is separated and the aqueous solution is further extracted with methylene chloride (100 mL). The combined organic solutions are dried (Na$_2$SO$_4$) and concentrated to dryness. The obtained solid is suspended in n-hexane (100 mL) for 1 hour and filtered to give a 9:1 mixture ($^1$H-NMR evaluation) of 9-fluoro-6-(p-toluenesulfonyloxy) benzo[g]isoquinoline-5,10-dione and 9-chloro-6-(p-toluenesulfonyloxy)benzo[g]isoquinoline-5,10-dione respectively (8.85 g).

m.p.: 156°–158° C.

Preparative Example 11

3-(5-chloro-2-fluorobenzoyl)isonicotinic Acid and 4-(5-chloro-2-fluorobenzoyl)nicotinic Acid Sec-butyllithium (1.3M in cyclohexane; 6.0 mL) is added dropwise via a syringe to a stirred solution of 1-chloro-4-fluorobenzene (0.97 g) in THF (70 mL) at −75° C. which is kept under a nitrogen atmosphere. After stirring for additional 30 min, the yellow mixture is transferred dropwise via a jacketed canula into a stirred mixture of pyridine-3,4-dicarboxylic acid anhydride (1.00 g) in THF (100 mL) at −78° C. under a nitrogen blanket. The pale yellow solution is allowed to warm to −20° C. for 4 hours. The THF is removed at reduced pressure. The yellow solid obtained is dissolved in water (10 mL), cooled to 0° C., and acidified with dilute HCl in an ice-bath and the resulting precipitate is collected by filtration. Upon heating the white solid with acetone (30 mL), an insoluble material remains (0.095 g), which by $^1$H-NMR analysis is a 94/4 mixture of 3-(5-chloro-2-fluorobenzoyl)isonicotinic acid and 4-(5-chloro-2-fluorobenzoyl)nicotinic acid, respectively.

m.p.: 289°–291° C.

After centrifugation, the supernate is removed and roto-evaporated to give crystals of a 94/6 mixture (by $^1$H-NMR analysis) of 4-(5-chloro-2-fluorobenzoyl)nicotinic acid and 3-(5-chloro-2-fluorobenzoyl)isonicotinic acid respectively (0.947 g).

m.p.: 236°–237° C.

Sublimation of this mixture (0.025 g) at 180°–205° C./0.5 mm Hg gives a white solid with a 98/2 ratio of 4-(5-chloro-2-fluorobenzoyl)nicotinic acid and 3-(5-chloro-2-fluorobenzoyl) isonicotinic acid respectively (20 mg).

4-(5-chloro-2-fluorobenzoyl)nicotinic acid: $^1$H-NMR (CDCl$_3$/CD$_3$OD 9/1): 6.96 (m, 1H); 7.21 (d, 1H); 7.45 (m, 1H); 7.86 (m, 1H); 8.76 (d, 1H); 9.18 (s, 1H).

3-(5-chloro-2-fluorobenzoyl)isonicotinic acid: $^1$H-NMR (DMSO-d$_6$): 7.37 (m, 1H); 7.75 (m, 2H); 7.83 (d, 1H); 8.77 (s, 1H); 8.90 (d, 1H).

Preparative Example 12

4-(5-chloro-2-fluorobenzyl)nicotinic Acid

Zinc-copper couple (0.75 g) is added to a stirred mixture of 4-(5-chloro-2-fluorobenzoyl)nicotinic acid and 3-(5-chloro-2-fluorobenzoyl)isonicotinic acid of Preparative Example 11 (94/6 on a molar base; 0.60 g) in 75% formic acid. The exothermic and effervescent reaction mixture is stirred for 15 min before heating to 80° C. for 2 hours. After cooling to 40° C., the mixture is filtered through a sintered glass funnel. The solid is washed with 75% formic acid (1×5 mL) and ethyl acetate (2×5 mL). The mixture is concentrated by roto-evaporation to about 2 mL. The orange oil obtained is dissolved in 0.5N HCl (3 mL) and extracted with ethyl acetate (3×10 mL), then saturated with NaCl and extracted with ethyl acetate/1,2-dimethoxyethane (2×5 mL). The combined extracts are dried with Na$_2$SO$_4$ and the solvents removed by roto-evaporation to yield a yellow foam. The foam (0.541 g) is recrystallized in hot acetonitrile (1 mL) to yield 4-(5-chloro-2-fluorobenzyl)nicotinic acid (0.142 g).

m.p.: 174°–176° C.

$^1$H-NMR (CDCl$_3$/CD$_3$OD 9/1): 4.43 (s, 2H); 6.79 (m, 1H); 6.86 (m, 1H); 6.95 (m, 1H); 7.11 (d, 1H); 8.55 (d, 1H); 9.12 (s, 1H).

Preparative Example 13

9-chloro-6-fluorobenzo[g]isoquinoline-5,10-dione

Fuming sulfuric acid (30% SO$_3$; 0.31 mL) is added to 4-(5-chloro-2-fluorobenzyl)nicotinic acid of Preparative Example 12. The dark mixture is heated quickly to 130° C. for 10 min in a flask fitted with a cotton filled drying tube. After cooling to room temperature, the reaction mixture is quenched with ice (3 g) and extracted with methylene chloride (4×7 mL). The combined extracts are dried with Na$_2$SO$_4$ and the solvent is removed by roto-evaporation to yield 9-chloro-6-fluorobenzo[g]isoquinoline-5,10-dione as a yellow solid (0.045 g; 82% yield).

m.p.: 204°–206° C.

$^1$H-NMR (CDCl$_3$): 7.45 (m, 1H); 7.83 (m, 1H); 7.98 (d, 1H); 9.08 (d, 1H); 9.49 (s, 1H).

Example 1

5-(p-toluenesulfonyloxy)-2-methylisoquino[8,7,6-cd]indazole-6(2H)-one

The 1:1 mixture of 9-fluoro-6-(p-toluenesulfonyloxy)benzo[g]isoquinoline-5,10-dione and 9-chloro-6-(p-toluenesulfonyloxy)benzo[g]isoquinoline-5,10-dione, of Preparative Example 10a, (0.041 g) is dissolved in dry pyridine (2 mL) and a freshly prepared 1M solution of N-methylhydrazine in pyridine (0.183 mL) is added. After stirring for three hours at room temperature the reaction mixture is concentrated to dryness and added with water (5 mL), with NaH$_2$PO$_4$ saturated solution (5 mL) and extracted several times with methylene chloride (50 mL). The combined organic solutions are dried ever anhydrous sodium sulfate and the solvent is removed at reduced pressure. The obtained residue is purified by silica-gel column chromatography (eluant: methylene chloride/ethyl acetate 90/10 v/v (50 mL), then 75/25 (50 mL), then 60/40 (50 mL) and finally 40/60 (50 mL) to give 2-methyl-5-(p-toluenesulfonyloxy)isoquino [8,7,6-cd]indazole-6(2H)-one.

$^1$H-NMR (CDCl$_3$): 2.42 (s, 3H); 4.25 (s, 3H); 7.33 (d, 2H); 7.53 (d, 1H); 7.63 (d, 1H); 7.95 (d, 2H); 8.07 (d, 1H) 8.80 (d, 1H); 9.50 (s, 1H).

Example 2

2-[2-(dimethylamino)ethyl)]-5-(p-toluenesulfonyloxy)isoquino[8,7,6-cd]indazole-6(2H)-one Under a nitrogen atmosphere a solution of 2-(dimethylaminoethyl)hydrazine (J. Med. Chem. 7, 493, 1964) (1.86 g) in anhydrous THF (6.0 mL) is added during 30' to the stirred 9:1 mixture of 9-fluoro-6-(p-toluenesulfonyloxy)benzo[g]isoquinoline-5,10-dione and 9-chloro-6-(p-toluenesulfonyloxy)benzo[g]isoquinoline-5,10-dione of Preparative Example 10b (2.4 g) in THF (24 mL) containing N,N-diisopropylethylamine (1.10 mL). A slightly exothermic reaction ensues, and the reaction temperature increases from 20° C. to 25° C. After one hour at room temperature the reaction mixture is poured in water (240 mL) and the suspension obtained is stirred for 30'. The solid is separated by suction, washed with water and dried at 40° C. to give 2-[2-(dimethylamino)ethyl)]-5-(p-toluenesulfonyloxy)isoquino[8,7,6-cd]indazole-6(2H)-one (1.44 g).

m.p.: 139°–141° C.

$^1$H-NMR (CDCl$_3$): 2.35 (s, 6H); 2.45 (s, 3H); 2.95 (t, 2H); 4.65 (t, 2H); 7.35 (d, 2H); 7.52 (d, 1H); 7.80 (d, 1H); 7.95 (d, 2H); 8.10 (d, 1H); 8.80 (d, 1H); 9.55 (s, 1H).

Example 3

2-[2-(N-tert-butoxycarbonylamino)ethyl]-5-(p-toluenesulfonyloxy)isoquino[8,7,6-cd]indazole-6(2H)-one (2-N-tert-butoxycarbonylaminoethyl)hydrazine is prepared by reaction of N-t-butoxycarbonyl-2-chloroethylamine with hydrazine following a procedure adapted from J. Med. Chem. 7, 493, (1964). Under a nitrogen atmosphere a solution of (2-N-tert-butoxycarbonylaminoethyl)hydrazine (9.2 g) in anhydrous THF (10 mL) is added during 30' to the stirred 9:1 mixture of 9-fluoro-6-(p-toluenesulfonyloxy)benzo[g]isoquinoline-5,10-dione and 9-chloro-6-(p-toluenesulfonyloxy)benzo [g]isoquinoline-5,10-dione of Preparative Example 10b (3.0 g) in THF (25 mL) containing N,N-diisopropylethylamine (1.38 mL). A slightly exothermic reaction ensues, and the reaction temperature increases from 21° C. to 24° C. After stirring for one hour at room temperature the obtained precipitate is recovered by suction, washed with THF/n-hexane 1/1 (15 mL) and dried at 40° C. under vacuum, to give 2-[2-(N-tert-butoxycarbonylamino)ethyl]-5-(p-toluenesulfonyloxy)isoquino [8,7,6-cd]indazole-6(2H)-one (1.33 g).

m.p.: 206°–208° C.

$^1$H-NMR (CDCl$_3$): 1.4 (s, 9H); 2.45 (s, 3H); 3.75 (q, 2H); 4.70 (t, 2H); 4.92 (br, 1H); 7.35 (d, 2H); 7.50 (d, 1H); 7.75 (d, 1H); 7.95 (d, 2H); 8.09 (d, 1H); 8.78 (d, 1H); 9.50 (s, 1H).

Example 4

2-[2-[(2-hydroxyethyl)amino]ethyl]-5-(p-toluenesulfonyloxy)isoquino[8,7,6-c]indazole-6(2H)-one A solution of 2-[(2-hydroxyethylamino)ethyl]hydrazine (J. Het. Chem., 26, 85, (1989); 0.179 g) in absolute ethanol (0.5 mL) is dropped into a stirred solution of the 9:1 mixture of 9-fluoro-6-(p-toluenesulfonyloxy)benzo[g]isoquinoline-5,10-dione and 9-chloro- 6-(p-toluenesulfonyloxy)benzo[g]isoquinoline-5,10-dione of Preparative Example 10b (0.200 g) in THF (2.0 mL) containing triethylamine (0.073 mL). After stirring for 2 hours at room temperature an additional amount of 2-[(2-hydroxyethylamino)ethyl]hydrazine (0.179 g) in absolute ethanol (0.5 mL) is added and after two additional hours the reaction mixture is concentrated to the volume of about 1 mL. Water (20 mL) is added and the mixture is allowed to stir at room temperature overnight. The precipitate is collected by suction filtration, dried under vacuum at 40° C. and finally sludged in boiling ethyl acetate to give 2-[2-[(2-hydroxyethyl)amino]ethyl]-5-(p-toluenesulfonyloxy) isoquino[8,7,6-c]indazole-6(2H)-one (0.060 g).

m.p.: 131°–133° C.

$^1$H-NMR (DMSO-d$_6$/D$_2$O): 2.45 (s, 3H); 2.62 (t, 2H); 3.13 (t, 2H); 3.40 (t, 2H); 4.65 (t, 2H); 7.25 (d, 1H); 7.40 (d, 2H); 7.75 (d, 2H); 7.95 (d, 1H); 8.15 (d, 1H); 8.80 (d, 1H); 9.40 (s, 1H).

Example 5

Preparation of 2-(aminoalkyl)-5-(p-toluenesulfonyloxy)isoquino[8,7,6-cd]indazole-6(2H)-ones Using the procedure of Examples 1–4, the following compounds are obtained by reaction of the mixtures of 9-fluoro-6-(p-toluenesulfonyloxy)benzo[g]isoquinoline-5,10-dione and 9-chloro-6-(p-toluenesulfonyloxy)benzo[g]isoquinoline-5,10-dione of Preparative Example 10, with a substituted hydrazine selected from the group of 2-(diethylaminoethyl)hydrazine [J. Med. Chem., 7, 493, (1964)], 3-dimethylaminopropylhydrazine [J. Het. Chem., 23, 1491, (1986)], 2-aminoethylhydrazine [J. Het. Chem., 23, 1491, (1986)], 2-(methylaminoethyl)hydrazine, 2-hydroxyethylhydrazine, 3-aminopropylhydrazine [J. Het. Chem., 23, 1491, (1986)];

2-[2-(diethylamino)ethyl]-5-(p-toluenesulfonyloxy)isoquino[8,7,6-cd]indazole-6(2H)-one;

2-[3-(dimethylamino)propyl]-5-(p-toluenesulfonyloxy)isoquino[8,7,6-cd]indazole-6(2H)-one;

2-[2-(amino)ethyl]-5-(p-toluenesulfonyloxy)isoquino[8,7,6-cd]indazole-6(2H)-one;

2-[2-(methylamino)ethyl]-5-(p-toluenesulfonyloxy)isoquino[8,7,6-cd]indazole-6(2H)-one;

2-[3-(amino)propyl]-5-(p-toluenesulfonyloxy)isoquino[8,7,6-cd]indazole-6(2H)-one.

Example 6

5-chloro-2-methylisoquino[5,6,7-cd]indazole-6(2H)-one

A solution of methyl hydrazine (0.76M; 0.021 g) in pyridine (0.6 mL) is added dropwise over two min to a stirred solution of 9-chloro-6-fluorobenzo[g]isoquinoline-5,10-dione of Preparative Example 13 in pyridine (0.5 mL) cooled with an ice-bath. A yellow precipitate appears in the dark solution after 6 min. After 1.3 h the reaction mixture is reduced to half its volume by a gentle stream of nitrogen and quenched with ice (5 g). The pale yellow precipitate is collected by suction filtration and washed with ice-water (2×1 mL) and dried under vacuum. The yellow solid is purified by silica gel column chromatography (eluant: chloroform/methanol 96/4 v/v) to yield 5-chloro-2-methylisoquino[5,6,7-cd]indazole-6(2H)-one (0.033 g; 71% yield) as a yellow solid.

m.p.: 244°–245° C.

$^1$H-NMR (CDCl$_3$): 4.25 (s, 3H); 7.59 (dd, 2H); 7.92 (d, 1H); 8.84 (d, 1H); 9.55 (s, 1H).

Example 7

Preparation of 2-(aminoalkyl)-5-chloroisoquino[5,6,7-cd]indazole-6(2H)ones

Using the procedure of Example 6 the following compounds are obtained by reaction of 9-chloro-6-fluorobenzo[g]isoquinoline-5,10-dione of Preparative Example 13 with a substituted hydrazine selected from the group of (2-N-tert-butoxycarbonylaminoethyl)hydrazine, 2-(dimethylaminoethyl) hydrazine [J. Med. Chem., 7, 493, (1964)], 2-(diethylaminoethyl)hydrazine [J. Med. Chem., 7, 493, (1964)], 2-[(2-hydroxyethylamino)ethyl]hydrazine (J. Het. Chem., 26, 85, (1989)], 3-dimethylaminopropylhydrazine [J. Het. Chem., 23, 1491, (1986)], 2-aminoethylhydrazine [J. Het. Chem., 23, 1491, (1986)], 2-(methylaminoethyl)hydrazine, 2-hydroxyethylhydrazine, 3-aminopropylhydrazine [J. Het. Chem., 23, 1491, (1986)];

2-[2-(N-tert-butoxycarbonylamino)ethyl)]-5-chloroisoquino [5,6,7-cd]indazole-6(2H)-one;
m.p.: 226°–228° C.
¹H-NMR (CDCl₃+CD₃OD): 1.30 (s, 9H); 3.58 (t, 2H); 4.63 (t, 2H); 7.54 (d, 1H); 7.70 (d, 1H); 7.90 (dd, 1H); 8.70 (d, 1H); 9.40 (s, 1H).

2-[2-(dimethylamino)ethyl]-5-chloroisoquino[5,6,7-cd]indazole-6(2H)-one;
m.p.: 160°–161° C.
¹H-NMR (CDCl₃): 2.32 (s, 6H); 2.95 (t, 2H); 4.65 (t, 2H); 7.60 (d, 1H); 7.69 (d, 1H); 8.00 (dd, 1H); 8.88 (d, 1H); 9.60 (s, 1H);

2-[2-(diethylamino)ethyl]-5-chloroisoquino[5,6,7-cd]indazole-6(2H)-one;

2-[2-(diethylamino)ethyl]-5-chloroisoquino[5,6,7-cd]indazole-6(2H)-one

2-[2-[(2-hydroxyethyl)amino]ethyl]-5-chloroisoquino[5,6,7-cd]indazole-6(2H)-one;
m.p.: 148°–152.5° C.
¹H-NMR (CDCl₃+CD₃OD): 2.75 (t, 2H); 3.43 (t, 2H); 3.60 (t, 2H); 4.63 (t, 2H) 7.55 (d, 1H); 7.75 (d, 1H); 7.98 (dd, 1H); 8.73 (d, 1H); 9.40 (s, 1H);

2-[3-(dimethylamino)propyl]-5-chloroisoquino[5,6,7-cd]indazole-6(2H)-one;

2-[2-(amino)ethyl]-5-chloroisoquino[5,6,7-cd]indazole-6(2H)-one;

2-[2-(methylamino)ethyl]-5-chloroisoquino[5,6,7-cd]indazole-6(2H)-one;

2-[2-(hydroxy)ethyl]-5-chloroisoquino[5,6,7-cd]indazole-6(2H)-one;

2-[3-(amino)propyl]-5-chloroisoquino[5,6,7-cd]indazole-6(2H)-one;

Example 8

5-[[2-(dimethylamino)ethyl]amino]-2-methylisoquino[8,7,6-cd]indazole-6(2H)-one

A 1M solution of N,N-dimethylethylenediamine in pyridine (0.10 mL) is added to a stirred suspension of 2-methyl-5-(p-toluenesulfonyloxy)isoquino[8,7,6-cd]indazole-6(2H)-one (0.02 g) in dry pyridine (2 mL). After stirring at room temperature for one hour the reaction mixture is heated at 70° C. for 13 hours while additional amounts of N,N-dimethylethylenediamine solution (0.1; 0.05; 0.05 mL) are added after 2, 4 and 11 hours respectively. Pyridine and excess N,N-dimethylethylenediamine are removed by distillation at reduced pressure and the obtained residue is partitioned between CH₂Cl₂ (50 mL) and brine (10 mL) to which NaHCO₃ saturated solution is added (1 mL). The organic solution is dried over anhydrous Na₂SO₄ and the solvent removed by distillation. The orange residue obtained is purified by silica-gel column chromatography (eluant: CHCl₃/MeOH 95/5 (30 mL) followed by CHCl₃/MeOH/NH₄OH 90/15/0.5 (50 mL) to give 2-methyl-5-[[2-(dimethylamino)ethyl]amino]isoquino[8,7,6-cd]indazole-6(2H)-one (0.011 g) as a reddish orange solid.
m.p.: 208°–215° C. (dec.).
¹H-NMR (CDCl₃): 2.40 (s, 3H); 2.75 (t, 2H); 3.57 (q, 2H); 4.25 (s, 3H); 6.97 (d, 1H); 7.63 (d, 1H); 8.30 (dd, 1H) 8.79 (d, 1H); 9.30 (br.t, 1H); 9.62 (d, 1H).

Example 9

2-[2-(dimethylamino)ethyl]-5-[[2-(dimethylamino)ethyl]amino]isoquino[8,7,6-cd]indazole-6(2H)-one A solution of 2-[2-(dimethylamino)ethyl]-5-(p-toluenesulfonyloxy)isoquino[8,7,6-cd]indazole-6(2H)-one of Example 2 (0.463 g) and 2-(dimethylamino)ethylamine (0.80 mL) in dry pyridine (4.63 mL) is heated at 80° C. for 1 h, 30' under a nitrogen blanket. The solution is then concentrated to dryness and the dark residue obtained is partitioned between brine (30 mL) and ethyl acetate (4×25 mL). The combined organic solutions are dried over Na₂SO₄ and concentrated to about 3 mL. After addition of n-hexane (12 mL) and stirring for one hour the precipitate is collected by suction and dried at 40° C. under vacuum to give 2-[2-(dimethylamino)ethyl)]5-[[2-(dimethylamino)ethyl] amino]isoquino[8,7,6-cd]indazole-6(2H)-one (0.23 g).
m.p.: 150°–152° C.
¹H-NMR (CDCl₃): 2.32 (s, 6H); 2.40 (s, 6H); 2.70 (t, 2H); 2.95 (t, 2H); 3.60 (q, 2H); 4.65 (t, 2H); 6.98 (d, 1H); 7.70 (d, 1H); 8.30 (d, 1H); 8.80 (d, 1H); 9.30 (br, 1H); 9.65 (s, 1H).

Example 10

2-[2-(N-tert-butoxycarbonylamino)ethyl]-5-[[2-(N-tert-butoxycarbonylamino)ethyl]amino]isoquino[8,7,6-cd]indazole-6(2H)-one A suspension of 2-[2-(N-tert-butoxycarbonylamino)ethyl]-5-(p-toluenesulfonyloxy)isoquino[8,7,6-cd]indazole-6(2H)-one of Example 3 (0.535 g) and N-(tert-butoxycarbonyl)ethylenediamine (prepared according to Synt. Comm., 20, 2559, (1990); 1.12 g) in dry pyridine (5.35 mL) is heated at 80° C. The dark solution obtained is held at this temperature for 5 hours, then it is concentrated to dryness and partitioned between brine (30 mL) and ethyl acetate (2×25 mL). The orange-red solid insoluble in the biphasic mixture is separated by suction filtration and dried at 40° C. under vacuum (0.43 g).

This material (0.60 g) is purified by column chromatography (SiO₂; eluant methylene chloride/methanol from 90/10 to 70/30 v/v). The fractions containing the product are pooled and concentrated to about 20 mL and 2-[2-(N-tert-butoxycarbonylamino)ethyl]-5-[[2-(N-tert-butoxycarbonylamino)ethyl]amino]isoquino[8,7,6-cd]indazole-6(2H)-one separates as red-orange crystals (0.45 g).
m.p.: 211°–213° C.
¹H-NMR (CDCl₃/DMSO-d₆ 9/1): 1.3 (s, 9H); 1.4 (s, 9H); 3.32 (q, 2H); 3.58 (m, 4H); 4.58 (t, 2H); 6.20 (br, 1H); 6.40 (br, 1H); 7.05 (d, 1H); 7.70 (d, 1H); 8.15 (d, 1H); 8.65 (d, 1H); 9.20 (br, 1H); 9.49 (s, 1H).

Example 11

2-[2-(N-tert-butoxycarbonylamino)ethyl]-5-[[(2-(dimethylamino)ethyl]amino]isoquino[8,7,6-cd]indazole-6(2H)-one A suspension of 2-[2-(N-tert-butoxycarbonylamino)ethyl]-5-(p-toluenesulfonyloxy) isoquino[8,7,6-cd]indazole-6(2H)-one (0.056 g) and 2-(dimethylamino)ethylamine (0.080 mL) in dry pyridine (0.50 mL) is heated at 80° C. The dark solution obtained is held at this temperature for 1 hour, then it is left at room temperature overnight. The dark precipitate obtained is separated by suction and purified by column chromatography (SiO₂; eluant ethyl acetate and then methylene chloride/methanol 9/0.5 v/v) to give 2-[2-(N-tert-butoxycarbonylamino)ethyl]-5-[[2-(dimethylamino)ethyl] amino]isoquino[8,7,6-cd]indazole-6(2H)-one (0.024 g) as a red-orange solid.
m.p.: 225°–227° C. (from methylene chloride).

$^1$H-NMR (CDCl$_3$): 1.43 (s, 9H); 2.40 (s, 6H); 2.7 (t, 2H); 3.55 (q, 2H); 3.78 (m, 2H); 4.65 (t, 2H); 5.23 (br.m, 1H); 6.87 (d, 1H); 7.62 (d, 1H); 8.28 (dd, 1H); 8.76 (d, 1H); 9.6 (s, 1H).

Example 12

Isoquino[8,7,6-cd]indazole-6(2H)-ones

Following the procedures of Examples 8–11, the following compounds are prepared by reaction of 2-[2-(dimethylamino)ethyl]-5-(p-toluenesulfonyloxy)isoquino[8,7,6-cd]indazole-6(2H)-one of Example 2, 2-[2-(N-tert-butoxycarbonylamino)ethyl]-5-(p-toluenesulfonyloxy)isoquino[8,7,6-cd]indazole-6(2H)-one of Example 3, or 2-[2-[(2-hydroxyethyl)amino]ethyl]-5-(p-toluenesulfonyloxy)isoquino[8,7,6-c]indazole-6(2H)-one of Example 4 with the properly selected amine:

2-[2-[(2-hydroxyethyl)amino]ethyl]-5-[[2-[(2-hydroxyethyl)amino]ethyl]amino]isoquino[8,7,6-cd]indazole-6(2H)-one;

$^1$H-NMR (CDCl$_3$): 3.25 (m, 6H); 3.61 (t, 4H); 3.71 (m, 4H); 3.98 (q, 2H); 4.65 (t, 2H); 5.31 (br, 2H); 7.08 (d, 1H), 7.70 (d, 1H); 8.30 (d, 1H); 8.83 (d, 1H); 9.30 (br, 1H); 9.69 (s, 1H).

2-[2-[(2-hydroxyethyl)amino]ethyl]-5-[[3-(amino)propyl]amino]isoquino[8,7,6-cd]indazole-6(2H)-one;

$^1$H-NMR (CDCl$_3$): 2.05 (m, 2H); 3.18 (m, 4H); 3.58 (t, 2H); 3.65 (t, 2H); 3.78 (q, 2H); 4.62 (t, 2H); 5.20 (br, 3H), 7.10 (d, 1H); 7.69 (d, 1H); 8.30 (d, 1H); 8.85 (d, 1H); 9.15 (br, 1H); 9.30 (t, 1H); 9.71 (s, 1H).

2-[2-[(2-hydroxyethyl)amino]ethyl]-5-[[2-(amino)ethyl]amino]isoquino[8,7,6-cd]indazole-6(2H)-one;

$^1$H-NMR (CDCl$_3$): 3.20 (m, 4H), 3.58 (t, 2H); 3.66 (t, 2H); 3.86 (q, 2H); 4.61 (t, 2H); 5.15 (br, 3H); 7.12 (d, 1H); 7.69 (d, 1H); 8.30 (d, 1H); 8.85 (d, 1H); 9.15 (br, 1H); 9.30 (t, 1H); 9.71 (s, 1H).

2-[2-[(2-hydroxyethyl)amino]ethyl]-5-[[2-(methylamino)ethyl]amino]isoquino[8,7,6-cd]indazole-6(2H)-one;

$^1$H-NMR (CDCl$_3$): 2.61 (s, 3H); 3.06 (t, 2H); 3.20 (t, 2H); 3.58 (t, 2H); 3.67 (t, 2H); 3.88 (q, 2H); 4.65 (t, 2H); 5.10 (t, 1H); 7.05 (d, 1H); 7.70 (d, 1H); 8.33 (d, 1H); 8.81 (d, 1H); 8.99 (br, 2H); 9.35 (t, 1H); 9.66 (s, 1H).

2-[2-[(2-hydroxyethylamino)ethyl]-5-[[2-(dimethylamino)ethyl]amino]isoquino[8,7,6-cd]indazole-6(2H)-one;

$^1$H-NMR (CDCl$_3$): 2.42 (s, 6H); 2.75 (t, 2H); 3.18 (t, 2H); 3.58 (q, 2H); 3.63 (t, 2H); 3.68 (t, 2H); 4.61 (t, 2H); 5.15 (t, 1H); 6.99 (d, 1H); 7.66 (d, 1H); 8.31 (d, 1H); 8.80 (d, 1H); 9.11 (br, 1H); 9.35 (t, 1H); 9.65 (s, 1H).

2-[2-[(2-hydroxyethyl)amino]ethyl]-5-[[2-(N-tert-butoxycarbonylamino)ethyl]amino]isoquino[8,7,6-cd]indazole-6(2H)-one;

$^1$H-NMR (CDCl$_3$+CD$_3$OD): 1.40 (s, 9H); 3.31 (m, 4H); 3.52 (q, 2H); 3.63 (t, 2H); 3.85 (t, 2H); 4.71 (t, 2H); 7.03 (d, 1H); 7.70 (d, 1H); 8.21 (dd, 1H); 8.76 (d, 1H); 9.61 (s, 1H).

2-[2-(N-tert-butoxycarbonylamino)ethy)]-5-[[2-[(2-hydroxyethyl)amino]ethyl]amino]isoquino[8,7,6-cd]indazole-6(2H)-one $^1$H-NMR (CDCl$_3$+CD$_3$OD): 1.45 (s, 9H); 3.18 (m, 4H); 3.73 (q, 2H); 3.80 (m, 4H); 4.67 (t, 2H); 7.00 (d, 1H); 7.68 (d, 1H); 8.25 (dd, 1H); 8.75 (d, 1H); 9.60 (s, 1H).

2-[2-(dimethylamino)ethyl]-5-[[2-[(2-hydroxyethyl)amino]ethyl]amino]isoquino[8,7,6-cd]indazole-6(2H)-one;

m.p.: 156°–157° C.

$^1$H-NMR (CDCl$_3$): 2.30 (s, 6H); 2.91 (m, 4H); 3.08 (t, 2H); 3.60 (t, 2H); 3.75 (m, 2H); 4.60 (t, 2H); 6.90 (d, 1H); 7.60 (d, 1H); 8.25 (dd, 1H); 8.75 (d, 1H); 9.45 (br, 1H); 9.60 (s, 1H).

2-[2-(dimethylamino)ethyl]-5-[[2-(amino)ethyl]amino]isoquino[8,7,6-cd]indazole-6(2H)-one;

$^1$H-NMR (CDCl$_3$+CD$_3$OD): 2.30 (s, 6H); 2.95 (t, 2H); 3.13 (t, 2H); 3.65 (t, 2H); 4.58 (t, 2H); 7.04 (d, 1H); 7.70 (d, 1H); 8.18 (dd, 1H); 8.66 (d, 1H); 9.51 (s, 1H).

Example 13

5-[[2-(dimethylamino)ethyl]amino]-2-methylisoquino[5,6,7-cd]indazole-6(2H)-one 5-chloro-2-methylisoquino[5,6,7-cd]indazole-6(2H)-one of Example 6 (0.013 g) is added to 2-(dimethylamino)ethylamine (0.34 mL). The yellow mixture is heated quickly to reflux for 1 hour. The excess diamine is removed from the orange solution by a gentle stream of nitrogen. The orange mixture obtained is purified by silica gel column chromatography with a gradient elution (1% methanol/chloroform (25 mL), 2% methanol/chloroform (25 mL), 4% methanol/chloroform (25 mL), 8% methanol/chloroform (25 mL), 12% methanol/chloroform (25 mL), 16% methanol/chloroform (25 mL), 24% methanol/chloroform (50 mL)) to yield 5-[[2-(dimethylamino)ethyl]amino]-2-methylisoquino[5,6,7-cd]indazole-6(2H)-one (0.010 g) as a reddish orange solid.

m.p.: 212°–216° C.

$^1$H-NMR (CDCl$_3$): 2.36 (s, 6H); 2.69 (t, 2H); 3.54 (q, 2H); 4.21 (s, 3H); 6.91 (d, 1H); 7.54 (d, 1H); 8.00 (d, 1H); 8.79 (d, 1H); 9.19 (br, 1H); 9.67 (s, 1H).

Example 14

2-[2-(dimethylamino)ethyl)]-5-[[2-(dimethylamino)ethyl]amino]isoquino[5,6,7-cd]indazole-6(2H)-one Under a nitrogen atmosphere N,N-dimethylethylenediamine (1.79 mL) is added to a stirred solution of 2-[2-(dimethylamino)ethyl]-5-chloroisoquino[5,6,7-cd]indazole-6(2H)-one (0.539 g) in pyridine (6.80 mL) and the resulting solution is heated at 80° C. for 12 hours. The pyridine and excess N,N-dimethylethylenediamine are removed by roto-evaporation and the obtained residue is purified by silica gel column chromatography eluting first with methylene chloride, then with methylene chloride/methanol 95/5 and finally with methylene chloride/methanol/concd. ammonia from 95/5/0.5 to 95/5/1 v/v/v. The fractions containing the yellow desired product are pooled and the solvents roto-evaporated. The obtained residue (0.529 g) is crystallized from diisopropylether to give 2-[2-(dimethylamino)ethyl)]-5-[[2-(dimethylamino)ethyl]amino]isoquino[5,6,7-cd]indazole-6(2H)-one as a yellow powder (0.291 g).

m.p.: 110°–111° C.

$^1$H-NMR (CDCl$_3$): 2.31 (s, 6H); 2.38 (s, 6H); 2.71 (t, 2H); 2.92 (t, 2H); 3.55 (q, 2H); 4.65 (t, 2H); 7.01 (d, 1H); 7.69 (d, 1H); 8.10 (dd, 1H); 8.83 (d, 1H); 9.30 (br.t., 1H); 9.71 (s, 1H).

Example 15

Isoquino[5,6,7-cd]indazole-6(2H)-ones

Using the procedures of Example 13 or 14, the following compounds are prepared by reaction of 2-[2-(N-tert-butoxycarbonylamino)ethyl]-5-chloroisoquino[5,6,7-cd]indazole-6(2H)-one, 2-[2-(dimethylamino)ethyl]-5-chloroisoquino[5,6,7-cd]indazole-6(2H)-one, or 2-[2-[(2-hydroxyethyl)amino]ethyl]-5-chloroisoquino[5,6,7-cd]indazole-6(2H)-one of Example 7:

2-[2-(N-tert-butoxycarbonylamino)ethyl]-5-[[2-(N-tert-butoxycarbonylamino)ethyl]amino]isoquino[5,6,7-cd]indazole-6(2H)-one;
m.p.: 211°–213° C.

$^1$H-NMR (CDCl$_3$): 1.40 (s, 9H); 1.46 (s, 9H); 3.55 (q, 2H); 3.65 (q, 2H); 3.77 (q, 2H); 4.69 (t, 2H); 5.55 (br, 2H); 7.00 (d, 1H); 7.60 (d, 1H); 7.93 (dd, 1H); 8.70 (d, 1H); 9.10 (br.t., 1H); 9.38 (s, 1H).

2-[2-(N-tert-butoxycarbonylamino)ethyl]-5-[[2-(amino)ethyl]amino]isoquino[5,6,7-cd]indazole-6(2H)-one; (reaction performed at 50° C. in DMSO as the solvent)
m.p.: 221°–222° C.

$^1$H-NMR (CDCl$_3$): 1.43 (s, 9H); 3.13 (t, 2H); 3.58 (q, 2H); 3.75 (q, 2H); 3.67 (t, 2H); 5.05 (br, 1H); 7.00 (d, 1H); 7.65 (d, 1H); 8.05 (dd, 1H); 8.60 (d, 1H); 9.30 (br., 1H); 9.75 (s, 1H).

2-[2-(N-tert-butoxycarbonylamino)ethyl)]-5-[[2-[(2-hydroxyethyl)amino]ethyl]amino]isoquino[5,6,7-cd]indazole-6(2H)-one;

$^1$H-NMR (CDCl$_3$+CD$_3$OD): 1.48 (s, 9H); 3.25 (m, 4H); 3.74 (q, 2H); 3.80 (m, 4H); 4.68 (t, 2H); 7.01 (d, 1H); 7.72 (d, 1H); 8.09 (dd, 1H); 8.80 (d, 1H); 9.75 (s, 1H).

2-[2-(N-tert-butoxycarbonylamino)ethyl)]-5-[[2-(dimethylamino)ethyl]amino]isoquino[5,6,7-cd]indazole-6(2H)-one;

$^1$H-NMR (CDCl$_3$): 1.44 (s, 9H); 2.31 (s, 6H); 2.75 (t, 2H); 3.68 (q, 2H); 3.75 (q, 2H); 4.68 (t, 2H); 5.10 (br.m.,H); 7.03 (d, 1H); 7.70 (d, 1H); 8.15 (dd, 1H); 8.85 (d, 1H); 9.33 (br.t., 1H); 9.71 (s, 1H).

2-[2-(dimethylamino)ethyl]-5-[[2-[(2-hydroxyethyl)amino]ethyl]amino]isoquino[5,6,7-cd]indazole-6(2H)-one;

$^1$H-NMR (CDCl$_3$+CD$_3$OD): 2.40 (s, 6H); 2.95 (t, 2H); 3.23 (m, 4H); 3.82 (m, 4H); 4.70 (t, 2H); 7.05 (d, 1H); 7.70 (d, 1H); 8.13 (dd, 1H); 8.85 (d, 1H); 9.70 (s, 1H).

2-[2-(dimethylamino)ethyl]-5-[[2-(amino)ethyl]amino]isoquino[5,6,7-cd]indazole-6(2H)-one;

$^1$H-NMR (CDCl$_3$): 2.39 (s, 6H); 2.95 (t, 2H); 3.15 (t, 2H); 3.68 (q, 2H); 4.68 (t, 2H); 7.00 (d, 1H); 7.65 (d, 1H); 8.12 (dd, 1H); 8.85 (d, 1H); 9.33 (br.t., 1H); 9.72 (s, 1H).

2-[2-[(2-hydroxyethyl)amino]ethyl]-5-[[2-[(2-hydroxyethyl)amino]ethyl]amino]isoquino[5,6,7-cd]indazole-6(2H)-one; (reaction performed at 52° C. in DMSO as solvent)
m.p.: 148°–151° C.

$^1$H-NMR (D$_2$O): 2.75 (m, 6H); 2.95 (m, 2H); 3.12 (m, 2H); 3.70 (m, 4H); 4.05 (m, 2H); 6.10 (d, 1H); 6.65 (d, 1H); 6.90 (d, 1H); 7.83 (s, 1H); 7.95 (d, 1H).

2-[2-[(2-hydroxyethyl)amino]ethyl]-5-[[2-(amino)ethyl]amino]isoquino[5,6,7-cd]indazole-6(2H)-one;

$^1$H-NMR (CDCl$_3$+CD$_3$OD): 2.97 (t, 2H); 3.30 (m, 4H); 3.68 (t, 2H); 3.85 (t, 2H); 4.66 (t, 2H); 7.00 (d, 1H); 7.69 (d, 1H); 8.10 (dd, 1H); 8.83 (d, 1H); 9.76 (s, 1H).

2-[2-[(2-hydroxyethyl)amino]ethyl]-5-[[3-(amino)propyl]amino]isoquino[5,6,7-cd]indazole-6(2H)-one;

$^1$H-NMR (CDCl$_3$+CD$_3$OD): 2.09 (m, 2H); 2.57 (t, 2H); 3.30 (m, 4H); 3.53 (t, 2H); 3.82 (t, 2H); 4.66 (t, 2H); 7.01 (d, 1H); 7.68 (d, 1H); 8.05 (dd, 1H); 8.80 (d, 1H); 9.68 (s, 1H).

2-[2-[(2-hydroxyethyl)amino]ethyl]-5-[[2-(methylamino)ethyl]amino]isoquino[5,6,7-cd]indazole-6(2H)-one;

$^1$H-NMR (CDCl$_3$+CD$_3$OD): 2.48 (s, 3H); 2.83 (t, 2H); 3.28 (m, 4H); 3.58 (t, 2H); 3.83 (t, 2H); 4.67 (t, 2H); 7.01 (d, 1H); 7.68 (d, 1H); 8.03 (dd, 1H); 8.80 (d, 1H); 9.67 (s, 1H).

2-[2-[(2-hydroxyethyl)amino]ethyl]-5-[[2-(dimethyamino)ethyl]amino]isoquino[5,6,7-cd]indazole-6(2H)-one;

$^1$H-NMR (CDCl$_3$+CD$_3$OD): 2.31 (s, 6H); 2.72 (t, 2H); 3.33 (m, 4H); 3.57 (t, 2H); 3.87 (t, 2H); 4.71 (t, 2H); 7.00 (d, 1H), 7.71 (d, 1H); 8.09 (dd, 1H); 8.81 (d, 1H); 9.70 (s, 1H)

2-[2-[(2-hydroxyethyl)amino]ethyl]-5-[[2-(N-tert-butoxycarbonylamino)ethyl]amino]isoquino[5,6,7-cd]indazole-6(2H)-one;

$^1$H-NMR (CDCl$_3$+CD$_3$OD): 1.41 (s, 9H); 3.29 (m, 4H); 3.56 (t, 2H); 3.79 (t, 2H); 3.83 (t, 2H); 4.68 (t, 2H); 7.05 (d, 1H); 7.68 (d, 1H); 8.08 (dd, 1H); 8.80 (d, 1H); 9.68 (s, 1H).

Example 16

Removal of the t-butoxycarbonyl Protective Group

Under a nitrogen atmosphere an ethanolic solution of anhydrous HCl (5N; 0.40 mL) is dropped into a stirred suspension of 2-[2-(N-tert-butoxycarbonylamino)ethyl]-5-[[2-(N-tert-butoxycarbonylamino)ethyl]amino]isoquino[8,7,6-cd]indazole-6(2H)-one of Example 10 (0.104 g) in absolute ethanol (2.1 mL). Initial dissolution of the starting material followed by precipitation of a dark-red solid is observed during the addition of ethanolic HCl. This solid is redissolved with absolute ethanol and the solution is heated to 40° C. for 2 h, 30'. The gradual formation of a red-amaranth precipitate is observed during the heating. After cooling to room temperature diethyl ether (10 mL) is added and the precipitate is collected by suction filtration under a nitrogen blanket, to give 2-[2-(amino)ethyl]-5-[[2-(amino)ethyl]amino]isoquino[8,7,6-cd]indazole-6(2H)-one trihydrochloride (0.070 g).

m.p.: 247°–250° C.

$^1$H-NMR (D$_2$O): 3.40 (t, 2H); 3.70 (t, 2H); 3.95 (t, 2H); 4.87 (t, 2H); 7.05 (d, 1H); 7.78 (d, 1H); 8.04 (dd, 1H); 8.62 (d, 1H); 9.10 (s, 2H).

UV (H$_2$O): $\lambda_{max}$ (E$_{1\%}$)=230 nm (650 cm); 240 nm (555 cm); 370 nm (244 cm); 591 nm (342 cm).

Example 17

Following the procedure of Example 16, the following compounds are prepared as the trihydrochloride salt starting from the appropriate N-tert-butoxycarbonyl derivatives of Examples 11, 12, 14, or 15:

2-[2-[(2-hydroxyethyl)amino]ethyl]-5-[[2-(amino)ethyl]amino]isoquino[8,7,6-cd]indazole-6(2H)-one;

$^1$H-NMR (D$_2$O): 3.07 (t, 2H); 3.39 (m, 4H); 3.69 (t, 2H); 3.88 (t, 2H); 4.83 (t, 2H); 7.05 (d, 1H); 7.70 (d, 1H); 8.33 (dd, 1H); 8.78 (d, 1H); 9.15 (s, 1H).

2-[2-(amino)ethyl)]-5-[[2-[(2-hydroxyethyl)amino]ethyl]amino]isoquino[8,7,6-cd]indazole-6(2H)-one;

$^1$H-NMR (D$_2$O): 3.28 (t, 2H); 3.31 (m, 4H); 3.85 (m, 4H); 4.90 (t, 2H); 7.03 (d, 1H); 7.70 (d, 1H); 8.35 (dd, 1H); 8.72 (d, 1H); 9.77 (s, 1H).

2-[2-(amino)ethyl)]-5-[[(2-(dimethylamino)ethyl]amino]isoquino[8,7,6-cd]indazole-6(2H)-one
m.p.: 224° C. (dec.).

$^1$H-NMR (D$_2$O): 3.00 (s, 6H); 3.60 (t, 2H); 3.70 (t, 2H); 4.07 (t, 2H); 4.93 (t, 2H); 7.20 (d, 1H); 7.95 (d, 1H); 8.43 (dd, 1H); 8.77 (d, 1H); 9.43 (s, 1H).

UV (HCl 0.1N): $\lambda_{max}$ (E$_{1\%}$)=236 nm (485 cm); 382 nm (205 cm); 507 nm (232 cm).

2-[2-(amino)ethyl]-5-[[2[(amino)ethyl]amino]isoquino[5,6,7-cd]indazole-6(2H)-one
m.p.: >260° C.

$^1$H-NMR (D$_2$O): 3.42 (t, 2H); 3.75 (t, 2H); 4.00 (t, 2H); 5.05 (t, 2H); 7.32 (d, 1H); 8.09 (d, 1H); 8.62 (d, 1H); 8.87 (d, 1H); 9.55 (s, 1H)

UV (HCl 0.1N): $\lambda_{max}$ (E$_{1\%}$)=245 nm (622 cm); 275 nm (181 cm); 351 nm (258 cm); 472 nm (327 cm), 494 nm (353 cm).

2-[2-(amino)ethyl)]-5-[[-[(2-hydroxyethyl)amino]ethyl]amino]isoquino[5,6,7-cd]indazole-6(2H)-one;

2-[2-(amino)ethyl)]-5-[[2-(dimethylamino)ethyl]amino]isoquino[5,6,7-cd]indazole -6(2H)-one;

Example 18

2-[2-(dimethylamino)ethyl]-5-[[2-(amino)ethyl]amino]isoquino[8,7,6-cd]indazole-6(2H)-one Dimaleate A solution of maleic acid (0.030 g) in absolute ethanol (0.4 mL) is added drop-wise into a stirred solution of 2-[2-(dimethylamino)ethyl]-5-[[2-(amino)ethyl]amino]isoquino[8,7,6-cd]indazole-6(2H)-one of Example 12 (0.030 g) in absolute ethanol (1.5 ml) held at 50° C. After the addition is complete the reaction mixture is maintained at 50° C. for 3 minutes and then allowed to cool to room temperature. After one hour the red-amaranth crystalline material which separated is filtered, washed with ethanol and dried under vacuum at 40° C. to give 2-[2-(dimethylamino)ethyl]-5-[[2-(amino)ethyl]amino]isoquino[8,7,6-cd]indazole-6(2H)-one dimaleate (0.029 g).

m.p.: 175°–175.5° C.

$^1$H-NMR (D$_2$O): 3.00 (s, 6H); 3.40 (t, 2H); 3.80 (t, 2H); 3.93 (t, 2H); 4.90 (t, 2H); 6.00 (s, 4H); 7.00 (d, 1H); 7.70 (d, 1H); 7.80 (d, 1H); 8.55 (d, 1H); 9.00 (s, 1H).

UV (HCl 0.1N): $\lambda_{max}$ (E$_{1\%}$)=236 nm (436 cm); 382 nm (169 cm); 507 nm (190 cm).

Example 19

Following the procedure of Example 18, the following maleate salts are prepared by salification of the appropriate isoquinoindazole-6(2H)-ones with maleic acid:

2-[2-(d imethylamino) ethyl) ]-5-[[2-(dimethylamino)ethyl]amino]isoquino[8,7,6-cd]indazole-6(2H)-one dimaleate
m.p.: 189°–191° C.

$^1$H-NMR (DMSO-d$_6$): 2.88 (s, 12H); 3.37 (t, 2H); 3.70 (t, 2H); 3.95 (q, 2H); 5.01 (t, 2H); 6.00 (s, 4H); 7.38 (d, 1H); 8.20 (dd, 1H); 8.85 (d, 1H); 9.20 (br.t., 1H); 9.55 (s, 1H).

UV (H$_2$O): $\lambda_{max}$ (E$_{1\%}$)=368 nm (154 cm); 469 nm (206 cm); 490 nm (211 cm).

2-[2-(dimethylamino)ethyl)]-5-[[2-(dimethylamino)ethyl]amino]isoquino[5,6,7-cd]indazole-6(2H)-one dimaleate
m.p.: 142°–146° C.

$^1$H-NMR (D$_2$O): 3.00 (s, 6H); 3.05 (s, 6H); 3.60 (t, 2H); 3.92 (t, 2H); 4.08 (t, 2H); 5.07 (t, 2H); 6.15 (s, 4H); 7.20 (d, 1H); 7.95 (d, 1H); 8.20 (d, 1H); 8.75 (d, 1H); 9.30 (s, 1H)

UV (H$_2$O): $\lambda_{max}$ (E$_{1\%}$)=292 nm (108 cm); 352 nm (133 cm); 476 nm (215 cm).

2-[2-(dimethylamino)ethyl]-5-[[2-[(2-hydroxyethyl)amino]ethyl]amino]isoquino[8,7,6-cd]indazole-6(2H)-one dimaleate
m.p.: 156°–157° C.

$^1$H-NMR (D$_2$O): 3.05 (s, 6H); 3.30 (m, 2H); 3.54 (t, 2H); 3.88 (m, 4H); 4.03 (t, 2H); 4.96 (t, 2H); 6.00 (s, 4H); 7.00 (d, 1H); 7.70 (d, 1H); 7.83 (dd, 1H); 8.57 (d, 1H); 9.05 (s, 1H)

UV (H$_2$O): $\lambda_{max}$ (E$_{1\%}$)=368 nm (1057 cm); 491 nm (210 cm).

We claim:
1. A compound according to the formula (I):

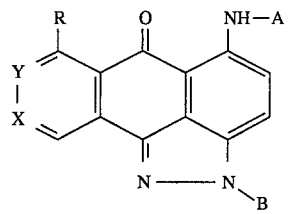

wherein R is hydrogen, X is carbon and Y is nitrogen;

A and B are the same or different and are selected from the group consisting of C$_1$–C$_{10}$ alkyl or phenylalkyl; C$_2$–C$_{10}$ alkyl having one or two substituents selected from the group consisting of OR$_1$ and NR$_2$R$_3$; C$_2$–C$_{10}$ alkyl interrupted by one or two oxygen atoms or by one —NR$_4$— group, said C$_2$–C$_{10}$ alkyl optionally substituted by one or two hydroxy or NR$_2$R$_3$ groups;

R$_1$ is selected from the group consisting of hydrogen, C$_1$–C$_6$ alkyl, phenyl, phenylalkyl, —S(O$_2$)R$_5$, C$_2$–C$_6$ alkyl optionally substituted by NR$_2$R$_3$;

R$_2$ and R$_3$ may be the same or different and are selected from the group consisting of hydrogen, C$_1$–C$_{10}$ alkyl, phenylalkyl, phenyl, C$_2$–C$_{10}$ alkyl substituted with one or two hydroxy groups, or R$_2$ and R$_3$ taken together with the nitrogen atom to which they are attached form an ethyleneimine ring or a 5- or 6-member aromatic or non-aromatic heterocyclic ring which optionally contains another heteroatom such as sulfur, oxygen or nitrogen;

R$_4$ is selected from the group consisting of hydrogen, C$_1$–C$_{10}$ alkyl, C$_2$–C$_{10}$ hydroxyalkyl, C$_2$–C$_{10}$ alkyl substituted by NR$_2$R$_3$, phenylalkyl, phenyl;

R$_5$ is selected from the group consisting of C$_1$–C$_{10}$ alkyl, phenylalkyl;

as free bases and their salts with pharmaceutically acceptable acids.

2. A compound according to claim 1 wherein said heterocyclic ring is selected from the group consisting of 1-imidazolyl, 1-pyrrolyl, 1-tetrahydropyrrolyl, 1-pyrazolyl, 4-morpholinyl, 1-piperidinyl, 1-piperazinyl, 1-(4-methyl)piperazinyl, and 1-(4-benzyl)-piperazinyl.

3. A compound according to claim 1 wherein A and B are independently selected from the group consisting of: —(CH$_2$)$_p$—NH$_2$ wherein p is the integer 2 or 3; —(CH$_2$)$_p$—NR$_2$R$_3$ wherein p is as above defined and R$_2$ and R$_3$ are methyl; —(CH$_2$)$_p$—NR$_2$R$_3$ wherein p is as above defined and R$_2$ is hydrogen and R$_3$ is methyl; —(CH$_2$)$_p$—OH wherein p is as above defined; —(CH$_2$)$_p$—NH—(CH$_2$)$_q$—OH wherein p and q are independently an integer selected from group consisting of 2 or 3.

4. The compound of claim 1 selected from the group consisting of

5-[[2-(dimethylamino)ethyl]amino]-2-methylisoquino[5,6,7-cd]indazole-6(2H)-one;

2-[2-(dimethylamino)ethyl)]-5-[[2-(dimethylamino)ethyl]amino]isoquino[5,6,7-cd]indazole-6(2H)-one;

2-[2-(dimethylamino)ethyl]-5-[[2-[(2-hydroxyethyl)amino]ethyl]amino]isoquino[5,6,7-indazole-6(2H)-one;

2-[2-(dimethylamino)ethyl]-5-[[2-(amino)ethyl]amino]isoquino[5,6,7-cd]indazole-6(2H)-one;

2-[2-[(2-hydroxyethyl)amino]ethyl]-5-[[2-[(2-hydroxyethyl)amino]ethyl]amino]isoquino ]5,6,7-cd]indazole-6(2H)-one;

2-[2-[(2-hydroxyethyl)amino]ethyl]-5-[[2-(amino)ethyl]amino]isoquino[5,6,7-cd]indazole-6(2H)-one;

2-[2-[(2-hydroxyethyl)amino]ethyl]-5-[[3-(amino)propyl]amino]isoquino[5,6,7-cd]indazole-6(2H)-one;

2-[2-[(2-hydroxyethyl)amino]ethyl]-5-[[2-(methylamino)ethyl]amino]isoquino[5,6,7-cd]indazole-6(2H)-one;

2-[2-[(2-hydroxyethyl)amino]ethyl]-5-[[2-(dimethyamino)ethyl]amino]isoquino[5,6,7-cd]indazole-6(2H)-one;

2-[2-(amino)ethyl]-5-[[2[(amino)ethyl]amino]isoquino[5,6,7-cd]indazole-6(2H)-one;

2-[2-(amino)ethyl)]-5-[[-[(2-hydroxyethyl)amino]ethyl]amino]isoquino[5,6,7-cd]indazole-6(2H)-one;

2-[2-(amino)ethyl)]-5-[[2-(dimethylamino)ethyl]amino]isoquino[5,6,7-cd]indazole-6(2H)-one; and 2-[2-(dimethylamino)ethyl)]-5-[[2-(dimethylamino)ethyl]amino]isoquino[5,6,7-cd]indazole-6(2H)-one dimaleate.

5. A pharmaceutical composition suitable for the treatment of tumors in a patient comprising a compound according to claim 1 and a pharmaceutically acceptable diluent or excipient.

6. A method of treatment of tumors susceptible to azaanthrapyrazole treatment in a mammal requiring such treatment comprising administering to the mammal an effective anti-tumor amount of a compound according to claim 1.

* * * * *

UNITED STATES PATENT AND TRADEMARK OFFICE
CERTIFICATE OF CORRECTION

PATENT NO. : 5,604,246

DATED : February 18, 1997

INVENTOR(S) : Krapcho et al.

It is certified that error appears in the above-indentified patent and that said Letters Patent is hereby corrected as shown below:

TITLE PAGE:

Item [75], line 3, delete "Verese" insert therefor -- Varese --

Signed and Sealed this

Thirteenth Day of May, 1997

Attest:

BRUCE LEHMAN

Attesting Officer     Commissioner of Patents and Trademarks